(12) United States Patent
Shiba et al.

(10) Patent No.: US 11,508,062 B2
(45) Date of Patent: Nov. 22, 2022

(54) OPHTHALMOLOGICAL IMAGE PROCESSING APPARATUS

(71) Applicant: NIDEK CO., LTD., Aichi (JP)

(72) Inventors: Ryosuke Shiba, Aichi (JP); Yoshiki Kumagai, Aichi (JP); Naoto Honda, Aichi (JP); Kenshiro Fujiu, Aichi (JP); Yuji Murase, Aichi (JP); Shohei Ito, Aichi (JP)

(73) Assignee: NIDEK CO., LTD., Aichi (JP)

( * ) Notice: Subject to any disclaimer, the term of this patent is extended or adjusted under 35 U.S.C. 154(b) by 264 days.

(21) Appl. No.: 16/830,936

(22) Filed: Mar. 26, 2020

(65) Prior Publication Data

US 2020/0311925 A1    Oct. 1, 2020

(30) Foreign Application Priority Data

Mar. 29, 2019    (JP) ............................ JP2019-067251
Mar. 29, 2019    (JP) ............................ JP2019-067252

(51) Int. Cl.
    *G06T 7/00*           (2017.01)
    *G06T 7/246*         (2017.01)
    (Continued)

(52) U.S. Cl.
    CPC .......... *G06T 7/0012* (2013.01); *A61B 3/0025* (2013.01); *A61B 3/102* (2013.01);
    (Continued)

(58) Field of Classification Search
    CPC ......... G06T 7/0012; G06T 5/003; G06T 5/50; G06T 7/248; G06T 2207/20201;
    (Continued)

(56) References Cited

U.S. PATENT DOCUMENTS 6,714,672 B1 * 3/2004 Berestov ................ G06V 40/19
                                          359/462
6,862,364 B1 * 3/2005 Berestov ................. G06T 5/008
                                           348/42
(Continued)

FOREIGN PATENT DOCUMENTS

EP          2184006 A1      5/2010
EP          2497410 A1 *  9/2012 ........... A61B 3/0058
(Continued)

OTHER PUBLICATIONS

Communication dated Aug. 4, 2020, from the European Patent Office in counterpart European Application No. 20165938.0.

*Primary Examiner* — Jose L Couso
(74) *Attorney, Agent, or Firm* — Sughrue Mion, PLLC

(57) ABSTRACT

An ophthalmological image processing apparatus acquires a plurality of images of a subject eye photographed in a scanning-type imaging optical system, sets any one of the plurality of images as a template, sets corresponding points or corresponding regions between an image of the subject eye and the template at a plurality of positions of each of the image of the subject eye and the template, calculates a movement amount of each of the corresponding points or each of the corresponding regions, and corrects a distortion of the image of the subject eye with respect to the template based on the movement amount of each of the corresponding points or each of the corresponding regions.

20 Claims, 21 Drawing Sheets

(51) Int. Cl.
*A61B 3/00* (2006.01)
*A61B 3/10* (2006.01)
*A61B 3/12* (2006.01)
*A61B 3/14* (2006.01)
*G06T 5/00* (2006.01)
*G06T 5/50* (2006.01)

(52) U.S. Cl.
CPC ............ *A61B 3/1225* (2013.01); *A61B 3/145* (2013.01); *G06T 5/003* (2013.01); *G06T 5/50* (2013.01); *G06T 7/248* (2017.01); *G06T 2207/20201* (2013.01); *G06T 2207/30041* (2013.01)

(58) Field of Classification Search
CPC . G06T 2207/30041; G06T 2207/10016; G06T 2207/10012; G06T 7/0016; G06T 7/32; G06T 7/33; A61B 3/0025; A61B 3/102; A61B 3/1225; A61B 3/145; A61B 3/1025; A61B 3/14; A61B 3/113; A61B 3/0058; A61B 5/7207; A61B 3/11; A61B 3/111; A61B 3/112; A61B 3/117; A61B 3/1173; A61B 3/1176; A61B 3/1216; A61B 3/13; G06V 2201/03; G06V 10/754; G06V 2201/12
See application file for complete search history.

(56) References Cited

U.S. PATENT DOCUMENTS

| | | |
|---|---|---|
| 9,232,887 B2 | 1/2016 | Goto et al. |
| 2007/0292037 A1* | 12/2007 | Allon ........................ G06T 7/33 382/238 |
| 2008/0225226 A1 | 9/2008 | Fujishiro et al. |
| 2010/0061601 A1* | 3/2010 | Abramoff ............ G06V 40/197 382/117 |
| 2010/0110171 A1 | 5/2010 | Satake |
| 2010/0110172 A1 | 5/2010 | Satake |
| 2011/0058029 A1* | 3/2011 | Nakajima ............ G06V 40/19 382/209 |
| 2011/0267581 A1* | 11/2011 | Nakajima .............. A61B 3/102 351/246 |
| 2013/0222566 A1 | 8/2013 | Murase |
| 2015/0002812 A1 | 1/2015 | Yoshihara et al. |

FOREIGN PATENT DOCUMENTS

| | | |
|---|---|---|
| EP | 2901919 A1 | 8/2015 |
| JP | 2008-228781 A | 10/2008 |
| JP | 2010-110392 A | 5/2010 |
| JP | 2013-015421 A | 1/2013 |
| JP | 2013-179972 A | 9/2013 |
| JP | 2015-8841 A | 1/2015 |
| JP | 2016-047100 A | 4/2016 |
| JP | 2016-123467 A | 7/2016 |
| WO | 2014103501 A1 | 7/2014 |

* cited by examiner

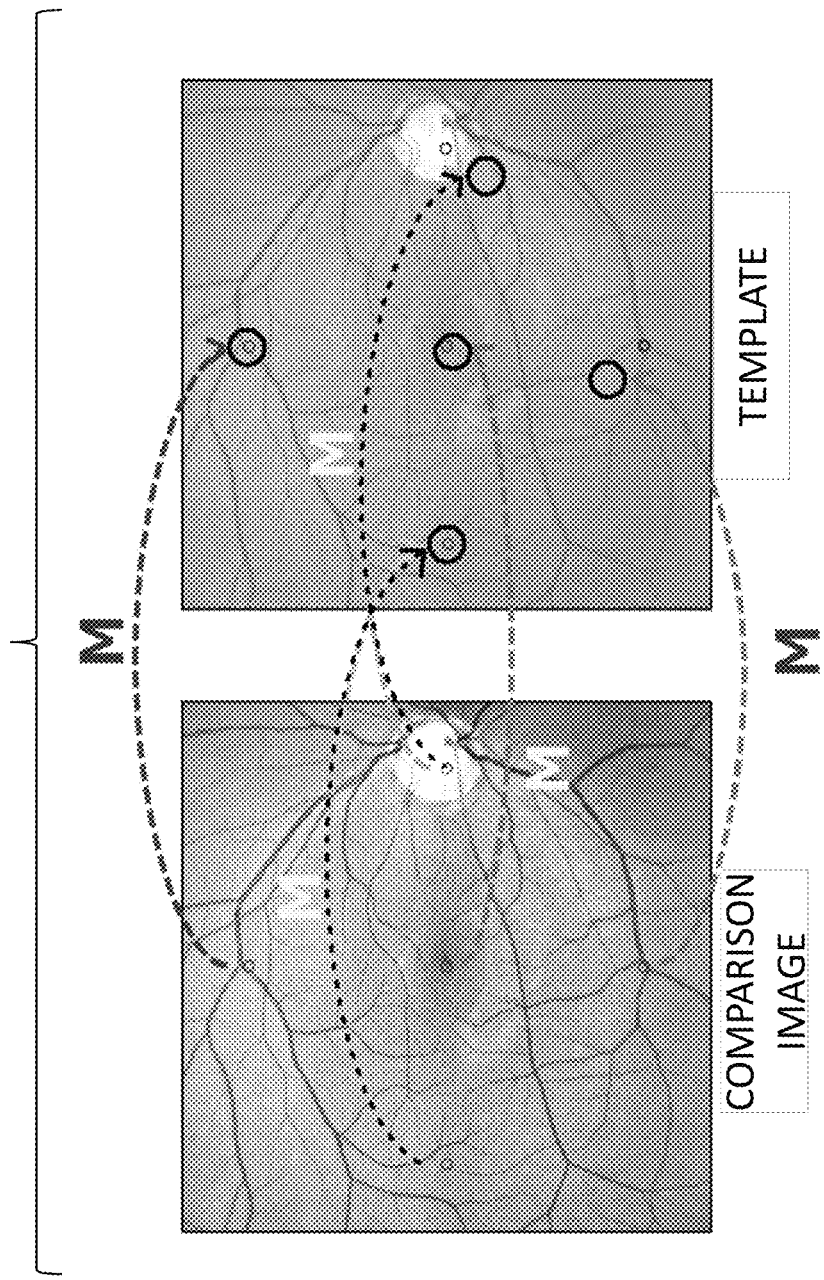

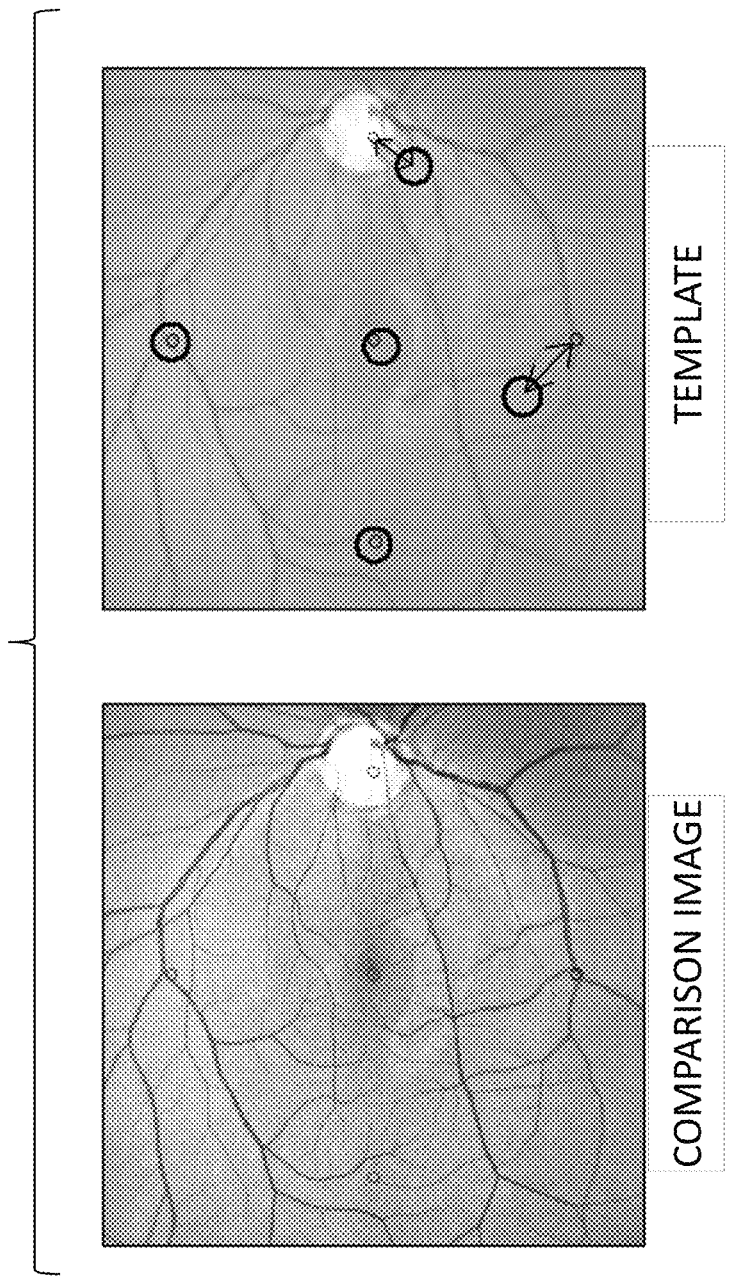

SECOND STAGE (SECOND LOOP)

OPHTHALMOLOGICAL IMAGE PROCESSING APPARATUS

CROSS-REFERENCE TO RELATED APPLICATION

This application claims priority from Japanese Patent Applications No. 2019-067251 filed on Mar. 29, 2019 and No. 2019-067252 filed on Mar. 29, 2019, the entire subject-matter of which is incorporated herein by reference.

TECHNICAL FIELD

The present disclosure relates to an ophthalmological image processing apparatus that processes an image of a subject eye.

BACKGROUND

In the related art, regarding the field of ophthalmology, there are known various techniques for improving image quality such as S/N by compositing a plurality of ophthalmologic images obtained by photographing the same place by image processing. Such a method is widely utilized, for example, in a tomographic image such as an OCT image in addition to a front image such as an SLO image (for example, see JP-A-2010-110392 and JP-A-2013-179972).

Further, the use of a scanning-type ophthalmologic imaging apparatus for photographing a subject eye with a wider angle of view has been rapidly spreading in recent years (for example, see JP-A-2016-123467).

Further, higher resolution is required for the scanning-type fundus imaging apparatus.

However, in the scanning-type imaging apparatus, as an image is photographed at a larger angle of view or higher resolution, the period of time required for photographing one image tends to increase. As the photographing time increases, it is difficult to avoid eye movement during photographing (scanning) of each image. That is, it is difficult to avoid distortion in each image. In such a case, it is difficult to cope with the method disclosed in patent literature 1.

SUMMARY

An object of the present disclosure is to provide an ophthalmological image processing apparatus which enables to obtain an image of a subject eye with less distortion.

An ophthalmological image processing apparatus according to the present disclosure is provided with the following configuration.

An ophthalmological image processing apparatus includes a processor, in which when an ophthalmological image processing program is executed by the processor, the processor executes:

acquisition processing of acquiring a plurality of images of a subject eye photographed by a scanning-type imaging optical system:

local matching of, by utilizing any one of the plurality of images of the subject eye as a template, setting corresponding points or corresponding regions between an image of the subject eye and the template at a plurality of positions of each of the image of the subject eye and the template, and calculating a movement amount of each of the corresponding points or each of the corresponding regions; and distortion correction processing of correcting a distortion of the image of the subject eye with respect to the template based on the movement amount of each of the corresponding points or each of the corresponding regions.

BRIEF DESCRIPTION OF DRAWINGS

FIG. 5C is a diagram for explaining affine transformation between each corresponding point on the template and each reference point on the comparison image.

FIG. 5D is a diagram for explaining the presence or absence of distortion based on the corresponding point and an affine mapping.

DETAILED DESCRIPTION

Hereinafter, an embodiment according to the present disclosure will be described with reference to the drawings. For convenience, hereinafter, unless otherwise specified, the processing content of the "ophthalmological image processing program" according to the embodiment will be described as being executed by an "ophthalmologic imaging apparatus".

The ophthalmologic imaging apparatus photographs a front image of a fundus (hereinafter, referred to as a fundus image) as an image of a subject eye (ophthalmologic image). However, the "ophthalmologic imaging apparatus" is not necessarily limited to the one that photographs the fundus, and may photograph another part such as an anterior part of a subject eye.

<Configuration of Apparatus>

The ophthalmologic imaging apparatus 1 (see FIG. 1) according to the embodiment includes at least imaging optical systems 10 and 20 (see FIG. 2) and an image processing device (image processing processor) 80. Hereinafter, the ophthalmologic imaging apparatus 1 is abbreviated as the present apparatus 1. By having the image processing device 80, the present apparatus 1 is a computer that executes various types of image processing. That is, it is an ophthalmological image processing apparatus. The image processing device 80 may be shared by a processor that controls an operation of the entire apparatus. The image processing device 80 may be separate from the processor that controls the operation of the entire apparatus. A memory accessible from a processor of the image processing device 80 may store an ophthalmological image processing program according to the embodiment.

Figure 1:
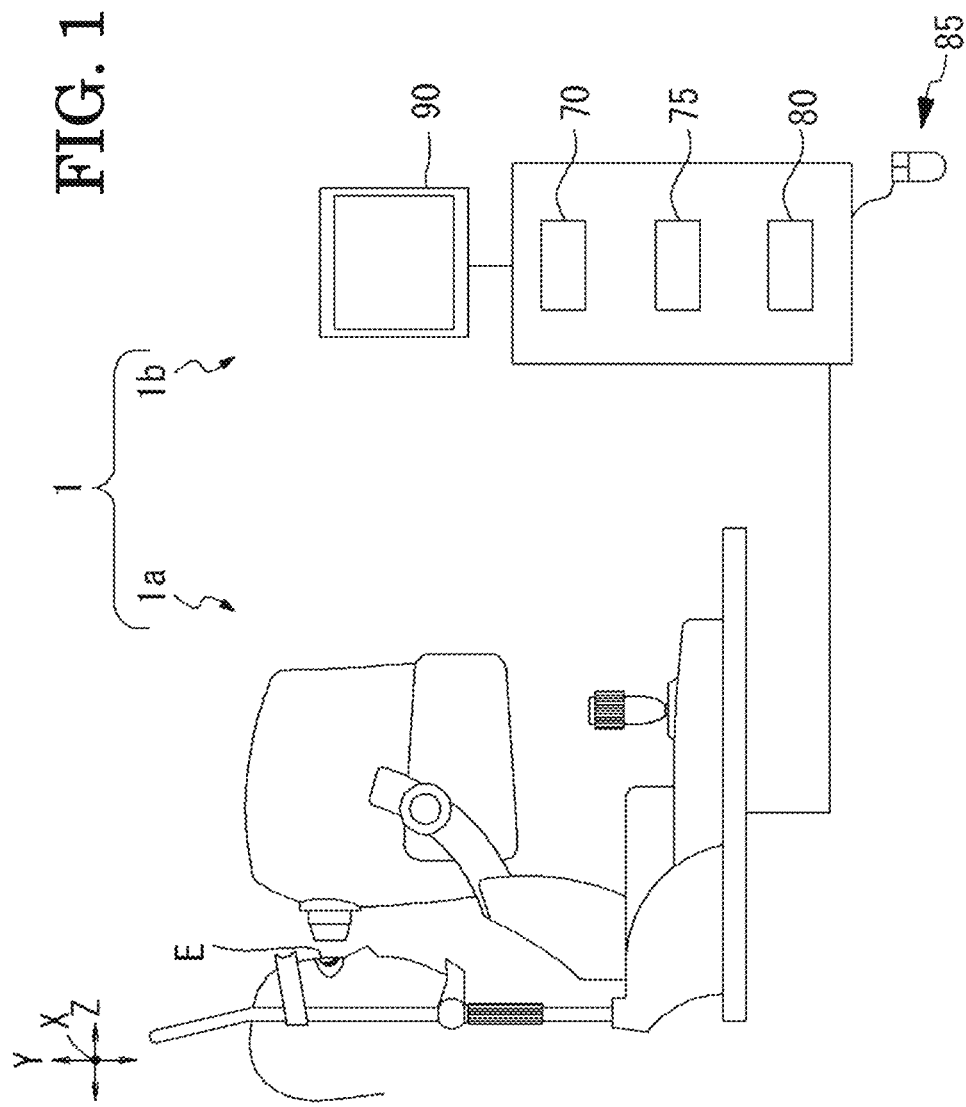
FIG. 1 is a diagram illustrating a schematic configuration of an apparatus according to an embodiment.

As illustrated in FIG. 1, for example, the present apparatus 1 is substantially divided into an optical unit 1a and a control unit 1b, and the imaging optical systems 10 and 20 may be stored in the optical unit 1a and the image processing device 80 may be stored in the control unit 1b, respectively. The control unit 1b has various types of memories 75 in addition to a processor (CPU) 70. The ophthalmological image processing program may be stored in the memory 75. Further, an operation portion 85 (user interface) may be connected to the control unit 1b. The operation portion 85 may be a pointing device such as a mouse and a touch panel, or may be another user interface. As the control unit 1b, for example, a PC may be utilized.

Further, the present apparatus 1 may have a monitor 90. On the monitor 90, for example, a photographed fundus image is displayed. In addition, various types of GUIs may be displayed on the monitor 90.

<Overview of Imaging Optical System>

The imaging optical systems 10 and 20 photograph fundus images. In the present embodiment, a front image of the fundus is photographed as a fundus image. However, it is not necessarily limited to this. The imaging optical systems 10 and 20 are substantially divided into an irradiation optical system 10 and a light receiving optical system 20 (see FIG. 2).

Figure 2:
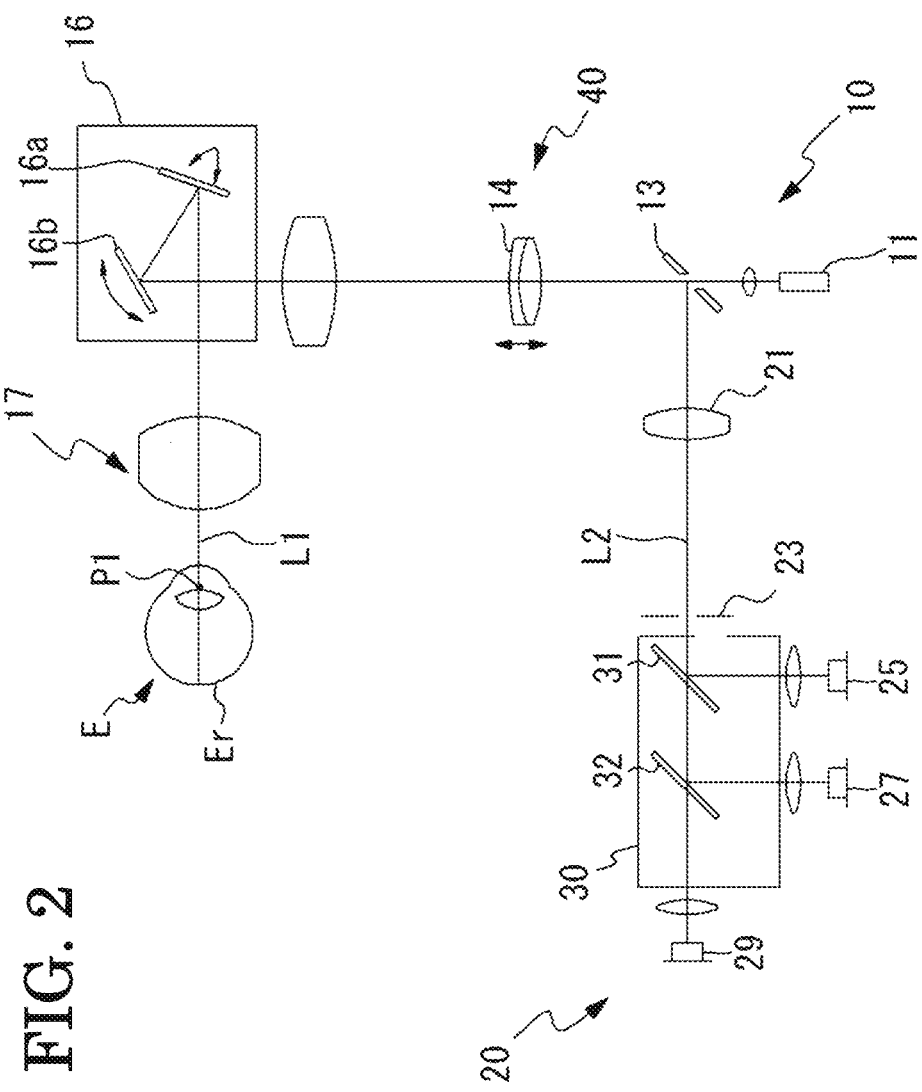
FIG. 2 is a diagram illustrating a schematic configuration of a imaging optical system.

The imaging optical systems 10 and 20 are scanning-type optical systems. The imaging optical systems 10 and 20 illustrated in FIG. 2 have a scanning portion 16 as an example of scanning means. The imaging optical systems 10 and 20 have three light receiving elements 25, 27, and 29 as a light receiving element. In FIG. 2, the imaging optical systems 10 and 20 are confocal optical systems.

Unless otherwise specified, the following description assumes that the imaging optical systems 10 and 20 are two-dimensional scan type optical systems. In the two-dimensional scan type, the illumination light is formed in a spot shape on the fundus and is two-dimensionally scanned on the fundus. However, it is not necessarily limited to this, and a line scan type (or slit scan type) optical system may be applied. In this case, the illumination light is formed in a line shape or a slit shape on the fundus, and the illumination light is scanned in a direction intersecting the cross-sectional longitudinal direction of the light flux of the illumination light.

<Irradiation Optical System>

First, the irradiation optical system 10 will be described. The irradiation optical system 10 has a scanning portion 16, condenses illumination light on the fundus in a point shape, and causes the scanning portion 16 to scan the illumination light on the fundus.

The scanning portion 16 (an example of the scanning means) scans the illumination light in two different directions. For convenience of explanation, in the following description, it is assumed that the illumination light is scanned by a raster scan. In this case, as illustrated in FIG. 2, the scanning portion 16 may include a first optical scanner 16a for main scanning and a second optical scanner 16b for sub-scanning. However, it is not limited to this, and the scanning portion 16 may be a device having two degrees of freedom (for example, MEMS). As the optical scanner, any one of a galvanometer mirror, a polygon mirror, a resonant scanner, a MEMS, an acousto-optic modulator (AOM), and the like may be appropriately selected.

The irradiation optical system 10 irradiates the fundus with the illumination light from a light source 11. The irradiation optical system 10 may be capable of simultaneously irradiating or may be capable of selectively switching and irradiating the fundus with light in a plurality of wavelength ranges.

Unless otherwise specified, in the following description, the irradiation optical system 10 will be described as irradiating visible light and infrared light.

The irradiation optical system 10 further includes a beam splitter 13, a lens 14, and an objective lens 17.

The beam splitter 13 couples and separates an optical path between the irradiation optical system 10 and the light receiving optical system 20. The beam splitter 13 may be a perforated mirror or another member.

The lens 14 is a focusing lens, and is displaced by a driving portion (not shown). The lens 14 and the driving portion are utilized as a focus adjustment portion 40 (diopter correction portion) in the present embodiment. In the present embodiment, the position of the lens 14 is controlled by a processor 70.

The objective lens 17 is an objective optical system of the present apparatus 1. The objective lens 17 is utilized to guide the laser light scanned by the scanning portion 16 to the fundus Er. The objective lens 17 forms a turning point P at a position of an exit pupil. At the turning point P, the illumination light passing through the scanning portion 16 is turned. The objective optical system may be a reflection system using a mirror instead of a refraction system like the objective lens 17.

The illumination light that has passed through the scanning portion 16 penetrates the objective lens 17, and thus passes through the turning point P. and the fundus Er is irradiated with the illumination light. By the illumination light is turned around the turning point P, the illumination light is scanned on the fundus Er. The illumination light with which the fundus Er is irradiated is reflected at a condensing position (for example, a retina surface). The fundus reflection light of the illumination light is emitted from a pupil as parallel light.

<Light Receiving Optical System>

Next, the light receiving optical system 20 will be described. The light receiving optical system 20 may have one or a plurality of light receiving elements. The light receiving optical system 20 guides the return light from the fundus Er to at least one of the light receiving elements 25, 27, and 29 to receive the light.

As illustrated in FIG. 2, in the light receiving optical system 20 in the present embodiment, each member disposed from the objective optical system 17 to the beam splitter 13 may be shared with the irradiation optical system 10. In this case, the light from the fundus Er goes back to the optical path of the irradiation optical system 10 and is guided to the beam splitter 13. The beam splitter 13 guides the light from the fundus Er to an independent optical path of the light receiving optical system 20.

Furthermore, the light receiving optical system 20 illustrated in FIG. 1 has a lens 21, a pinhole plate 23, and a light separating portion (light separating unit) 30 on the reflected optical path of the beam splitter 13.

The pinhole plate 23 is an example of a harmful light removing portion. Since the pinhole plate 23 is disposed on the fundus conjugated plane, the light from positions other than a focal point (or focal plane) of the fundus Er is removed, and the (light from the focal point) is guided to at least one of the three light receiving elements 25, 27, and 29.

The light separating portion 30 separates light from the fundus Er. In the present embodiment, the light from the fundus Er is wavelength-selectively separated by the light separating portion 30. Further, the light separating portion 30 may also serve as a light branching portion that branches the optical path of the light receiving optical system 20. For example, as illustrated in FIG. 2, the light separating portion 30 may include two dichroic mirrors (dichroic filters) 31 and 32 having different light separating characteristics (wavelength separation characteristics). The optical path of the light receiving optical system 20 is branched into three by two dichroic mirrors 31 and 32. Further, one of the light receiving elements 25, 27, and 29 is disposed at the end of each branched optical path.

For example, the light separating portion 30 separates the wavelength of light from the fundus Er, and causes the three light receiving elements 25, 27, and 29 to receive light in different wavelength ranges. For example, light of three colors of blue, green and red may be received by the light receiving elements 25, 27, and 29 one by one. In this case, a color image may be generated based on a light reception result of each of the light receiving elements 25, 27, and 29.

Further, the light separating portion 30 may cause different light receiving elements to receive the fluorescence from the fundus and the infrared light that is the fundus reflection light of the observation light. Thus, an infrared image may be photographed simultaneously with a fluorescent image. The fluorescent image may be a spontaneous fluorescent image or a contrast fluorescent image.

Since the above-described imaging optical systems 10 and 20 include a plurality of light receiving elements, each of the light receiving elements can simultaneously receive return light of a wavelength corresponding to each light receiving element. However, it is not necessarily limited to this. For example, as described in JP-A-2008-228781 by the present applicant, return light of different wavelength ranges is alternately (sequentially) received by one light receiving element, and thus the present disclosure is also applicable to an apparatus that acquires a fundus image based on a different wavelength range for each frame (or for each line).

<Switching the Angle of View>

The imaging optical systems 10 and 20 may have an angle of view-switching portion that changes the angle of view. For example, the angle of view switching portion may change the angle of view by switching an optical configuration of the objective optical system in the imaging optical systems 10 and 20. Specifically, the angle of view switching portion may include an insertion-removal mechanism for inserting or removing an optical element with respect to the objective optical system. As the optical element, a lens, a mirror, a prism, or the like can be used. Further, the angle of view switching portion may be a zoom mechanism that changes a refraction state by changing a positional relationship between two or more lenses along an optical path. Further, a refractive power variable lens such as a liquid crystal lens may be provided as an angle of view switching portion. Furthermore, the angle of view switching portion may include the scanning portion 16, and the angle of view may be switched by changing the swing angle of the optical scanners 16a and 16b The imaging optical systems 10 and 20 in the present embodiment may be capable of photographing a fundus image at an angle of view of 80° or more (with reference to the exit pupil). The angle of view switching portion may switch between a first angle of view of less than 80° and a second angle of view of 80° or more.

<Acquisition (Photographing) of Fundus Image>

The processor 70 forms a fundus image based on, for example, light receiving signals output from the three light receiving elements 25, 27, and 29. More specifically, the processor 70 forms a fundus image in synchronization with scanning (here, raster scanning) by the scanning portion 16.

In the present embodiment, by three light receiving elements 25, 27, and 29, three reading channels are formed. The processor 70 generates up to three types of images corresponding to the three read channels (hereinafter simply referred to as "channels") for each raster scan. In the present embodiment, various types of fundus images are generated by the image processing device 80.

The image processing device 80 may acquire, as an observation image, a fundus image of a plurality of frames which is sequentially formed based on an operation of the apparatus as described above. The observation image of each frame may be displayed on a monitor 90 in time series. The observation image is a moving image constituted by a fundus image acquired substantially in real time.

"Acquisition" in the present embodiment indicates that the fundus image is placed in a state that can be processed by the image processing device 80. For example, a fundus image is acquired by storing the fundus image in a predetermined memory region accessible by the image processing device 80.

Further, a part of the plurality of fundus images sequentially formed is taken (captured) as a photographed image (captured image). At that time, the photographed image is stored in a storage medium (for example, the memory 75). The storage medium on which the photographed image is stored may be a non-volatile storage medium (for example, a hard disk, a flash memory, or the like). In the present embodiment, for example, after a trigger signal (for example, a release operation signal or the like) is output, a fundus image formed at a predetermined timing (or period) is captured.

<Setting of Photographing Mode>

The processor 70 may change a photographing mode (a photographing method). The processor 70 may change at least one of the wavelength of the illumination light and the channel from which the light receiving signal is read out according to the photographing mode. The type of the fundus image acquired as the photographed image is changed according to the photographing mode. For example, in a first photographing mode, a color image may be acquired as a photographed image, and in a second photographing mode, a fluorescent image may be acquired as a photographed image.

Further, the insertion and removal of a filter (not shown) may be changed according to the photographing mode.

<Change of Required Time for Acquiring One Fundus Image>

The required time for acquiring one fundus image may be changeable. In this case, the required time is changed by the processor 70 controlling the scanning speed in the scanning portion 16. With the change in the required time, the number of pixels per one fundus image (in other words, the resolution) is changed. At this time, both the scanning speed in the main scanning direction and the in the sub-scanning direction may be controlled, or one of the scanning speed in the main scanning direction and in the sub-scanning direction may be controlled.

As an example, a fundus image may be formed with three types of pixels of 4096×4096 (substantially 0.6 sec), 1024× 1024 (substantially 0.14 sec), and 512×512 (substantially 0.07 sec). The values in parentheses are examples of the required time.

<Description of Operation>

Next, the operation of the present apparatus 1 when a fundus image is photographed will be described with reference to FIGS. 3 to 12.

Figure 3:
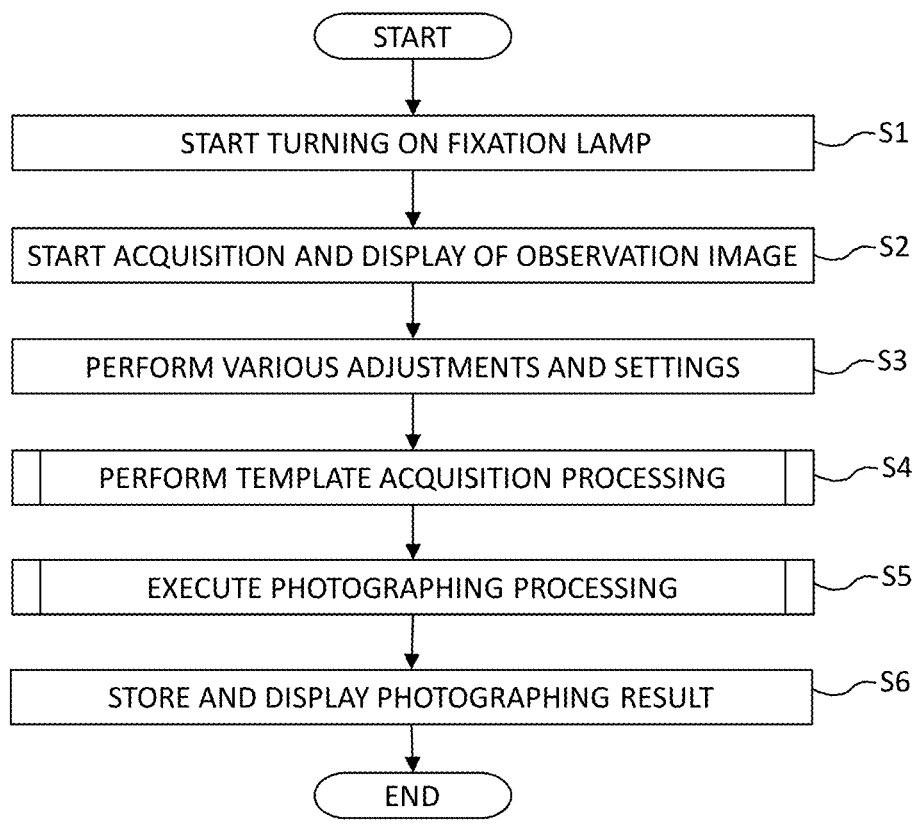
FIG. 3 is a flowchart illustrating a flow of an operation according to the embodiment.

As illustrated in FIG. 3, first, the processor 70 starts turning on the fixation lamp, and acquiring and displaying of an observation image (S1, S2). As the lighting control of the fixation lamp, the imaging optical systems 10 and 20 may be controlled such that visible light is temporarily turned on at a timing when light is scanned to a predetermined presentation position. In this way, an internal fixation lamp may be formed and presented to the subject eye. The observation image is preferably displayed at a higher frame rate. Therefore, the number of pixels in the observation image is set to a relatively small value (here, 512×512).

Further, various types of adjustments and settings are performed (S3). For example, the positional relationship between the subject eye and the apparatus may be adjusted, the focus state may be adjusted, or other adjustments may be performed. The adjustment may be manual or may be automatic. When the adjustment is manual, an examiner can refer to the observation image. Further, the processor 70 may set at least one condition among the photographing mode and the number of pixels in the photographed image based on the operation input from the examiner. The number of pixels of the photographed image may be set to a larger value as compared with that of the observation image.

Thereafter, template acquisition processing is performed (S4). By the template acquisition processing, a template serving as a reference image for positioning the photographed image is acquired. The template may be captured under a condition set in advance in the processing of S3. The template may be an image photographed under the same condition as the photographed image, or may be an image photographed under the condition different from the photographed image. Details of the template acquisition processing will be described later with reference to FIG. 4.

In a state where the template is acquired, the photographing processing (S5) is executed. The photographing processing is executed based on, for example, a trigger signal (for example, a release operation signal or the like). Details of the photographing processing will be described later with reference to FIG. 6. After the completion of the photographing processing (S5), the photographing result may be stored and displayed on the monitor 90 (S6). When the fundus image is properly photographed, the photographed image may be displayed as a photographing result. Further, when an error occurs during the photographing, the fact may be notified via the monitor 90.

<Template Acquisition Processings>

Figure 4:
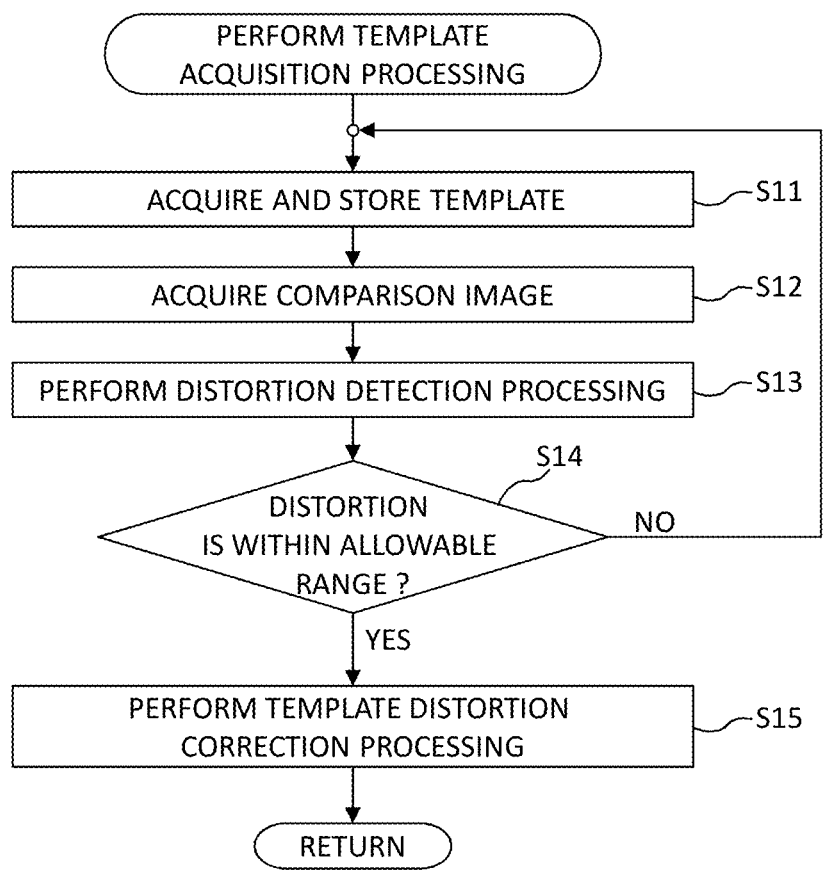
FIG. 4 is a flowchart for explaining a template acquisition processing.

Next, the template acquisition processing (S5) according to the embodiment will be described in detail with reference to FIG. 4. In the template acquisition processing, first, at least one fundus image is captured as a template (S11). The template is preferably a fundus image of the same type as the photographed image acquired by the photographing processing. Therefore, a capture may be executed as a template based on a trigger signal for starting photographing.

In the present embodiment, a comparison image (second template) is acquired at a timing different from a timing of capturing the template (S12). The comparison image is a fundus image photographed under the condition set so that distortion is smaller than that of the template. The comparison image is compared with the template by the image processing device 80, and distortion in the template is detected. Furthermore, in the present embodiment, the distortion in the template is corrected by the image processing device 80.

One example of the above condition is that the required time for acquiring the comparison image is shorter than the required time for acquiring the image serving as a template. In this case, the number of pixels of the comparison image may be smaller as compared with that of the template (and the photographed image). For example, the comparison image may be photographed with 512×512 pixels, while the template may be photographed with 1024×1024 or 4096× 4096 pixels.

Further, as another example of the above condition, the illumination light utilized for acquiring the comparison image is less likely to cause an examinee to feel dazzling than the illumination light utilized for acquiring the template. That is, the comparison image may be photographed under a condition set so that reflective eye movement due to dazzling is less likely to occur than when the template is photographed. As a specific example, the comparison image may be a fundus image using infrared light, and the template may be a fundus image using visible light. An observation image, which is one type of fundus image using infrared light, may be utilized as a comparison image. The photographing of the comparison image itself may be performed before the input of the trigger signal. For example, an observation image (or an added image using a plurality of observation images) captured in advance in a memory before the trigger signal is input may be used as the comparison image.

Further, the processing in S12 may include the photographing processing of the comparison image. In this case, the processor 70 photographs a fundus image serving as a comparison image by changing any of the above conditions with respect to the template. The required time for acquisition, the wavelength range of the illumination light, and a part or all of the channels may be different between the comparison image and the template. It is preferable that the photographing range of the comparison image is the same as the template and the photographed image, or includes the photographing range of the template and the photographed image.

<Specific Examples of Distortion Detection Processing and Determination Processing>

A specific example of the distortion detection processing (S13) and the determination processing (S14) will be described with reference to FIGS. 5A to 5D. In the specific example, the image processing device 80 obtains a plurality of corresponding points between the template and the comparison image, and detects a difference in displacement between each of the corresponding points as distortion.

Figure 5A:
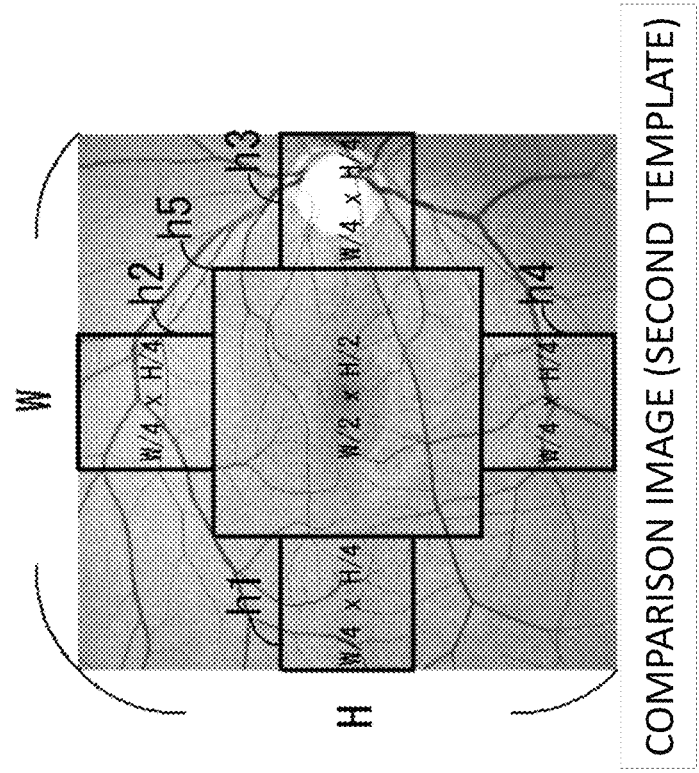
FIG. 5A is a diagram explaining a reference region (reference point) of a comparison image.

First, as illustrated in FIG. 5A, a plurality of reference regions are set in the comparison image. In FIG. 5A, regions h1 to h5 at different positions are utilized as reference regions. It is preferable that four or more reference regions are set.

Figure 5B:
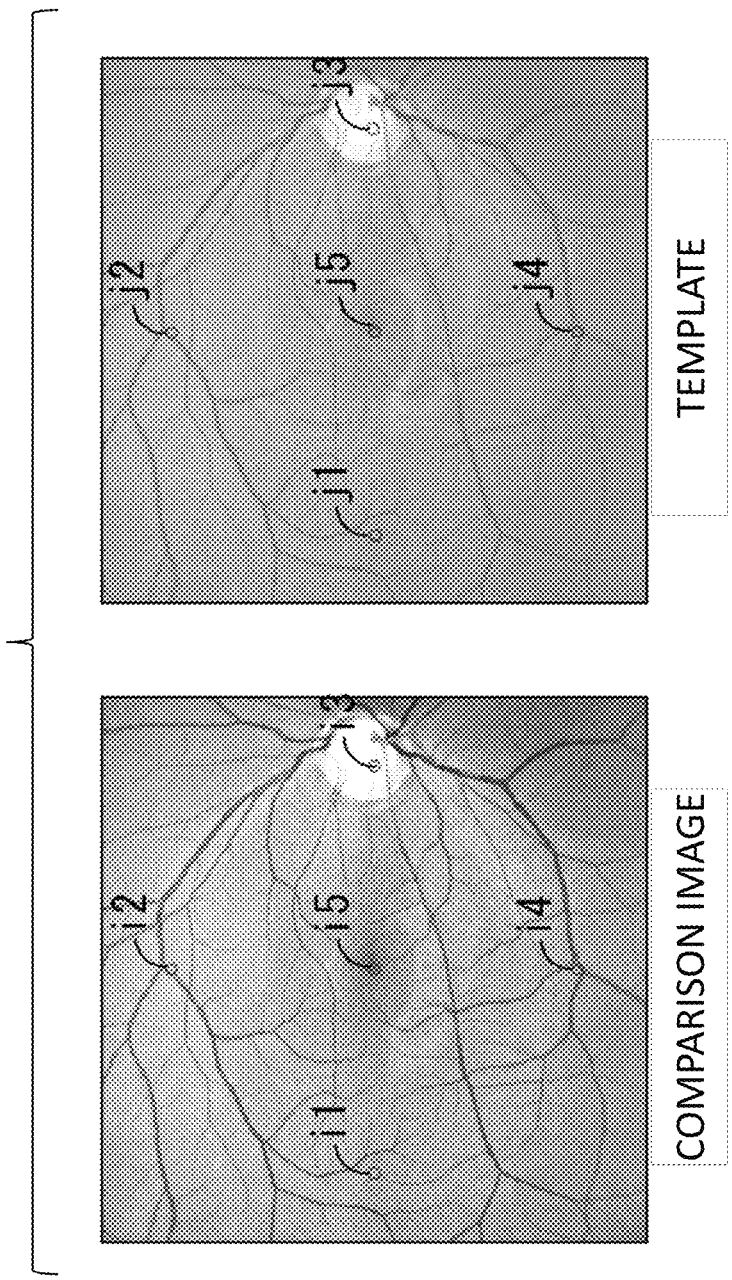
FIG. 5B is a diagram illustrating the reference point of the comparison image and a corresponding point specified on a template by matching the reference region.

In FIG. 5B, reference points i1 to i5 (corresponding points on the comparison image side) illustrated on the comparison image are the center points of the regions h1 to h5, respectively. The image processing device 80 obtains the corresponding points j1 to j5 corresponding to the reference points i1 to i5 on the template. The reference point and the corresponding point corresponding to the reference point are considered to indicate substantially the same position on the fundus. For example, the image processing device 80 performs matching for each of the regions h1 to h5 with respect to the template. In the matching, similarity degrees between each region of the template and each of the regions h1 to h5 is obtained. On the template, a region having the highest similarity degree with each of the regions h1 to h5 is a corresponding region to the regions h1 to h5. The corresponding points j1 to j5 are specified as the centers of each of the corresponding regions. For the matching, various processing such as a phase only correlation method can be applied.

"Matching" is image processing for obtaining a position where the similarity degree between two images (by obtaining a similarity degree map) is maximum (a threshold value or more). In various types of matching in the present embodiment, not only a phase only correlation (POC) but also various similarities may be utilized. For example, any one of SSD (Sum of Squared Difference), SAD (Sum of Absolute Difference), and normalized cross-correlation (NCC: Normalized Cross-Correlation, ZNCC: Zero-mean Normalized Cross-Correlation) may be utilized.

Next, the image processing device 80 obtains a transformation matrix M of the affine transformation between the reference points i1 to i5 and the corresponding points j1 to j5, and then maps each of the reference points i1 to i5 on the template using the transformation matrix M (see FIG. 5C). Since there are four or more reference points i1 to i5 and corresponding points j1 to j5 in each image, a transformation matrix M can be obtained. When an eye moves during photographing (specifically, when a movement changes), two-dimensional distortion occurs in the template. It is considered that the deviation between the mapping of the reference points i1 to i5 by the transformation matrix M and the corresponding points j1 to j5 increases in the region where the distortion occurred.

In FIG. 5C, five circles k1 to k5 are centered on the mapped point, and the size of the circle indicates the allowable range of distortion. When all the corresponding points j1 to j5 are included inside the circles k1 to k5, the image processing device 80 determines that the distortion is within the allowable range (S14: YES). On the other hand, since there are corresponding points j1 to j5 that are not included inside the circles k1 to k5, it is determined that the distortion is outside the allowable range (S14: NO). For example, FIG. 5D illustrates a template having a distortion out of the allowable range around corresponding points j3 and j4.

When it is determined that the distortion is out of the allowable range (S14: NO), in the example of FIG. 4, the template is acquired again (S11). The distortion of the re-acquired template is evaluated again in the above flow. This makes it possible to obtain a template in which the distortion with respect to the comparison image is within the allowable range. That is, it is possible to select an image closer to the comparison image photographed under the condition set so that the distortion is smaller than that of the template as the template. As a result, various types of processing of the photographed image based on the template are likely to be performed favorably.

However, when the distortion is out of the allowable range, in the first place, it is conceivable that the condition is not suitable for the subject eye, such as a subject eye that is difficult to fixate. That is, it is conceivable that the subject eye where the fixation is difficult to be stable is photographed. When a fundus image such as a template is newly photographed for such an eye under the same condition as the previous time, there is a possibility that the distortion in the new image is still out of the allowable range.

Therefore, when it is determined that the distortion is out of the allowable range (S14: NO), the processor 70 may photograph a fundus image (a third image in the present embodiment) under a condition set so as to reduce distortion (a third condition in the present embodiment). That is, the third image is photographed under the third condition in which distortion is unlikely to occur as compared with the template photographed in advance (one of the first images in the present embodiment). The third image may be a template (third template) acquired by re-photographing. Further, not only a template but also a fundus image composited based on the template may be used. Further, when the third image is used as a template, second distortion detection processing may be performed by the image processing device 80. The comparison image used in the second distortion detection processing may be a fundus image photographed under the condition set so as to have less distortion than the third image.

When it is determined that the distortion is out of the allowable range (S14: NO), the following processing may be performed instead of the re-photographing or together with the re-photographing. For example, photographing may be stopped. For example, when photographing is performed with visible light, by immediately stopping photographing, the burden on the examinee can be reduced. Further, in this case, in the processing in S6, the effect may be displayed on the monitor 90 as the photographing result.

However, even when it is determined that the distortion is out of the allowable range (S14: No), it is not always necessary to stop the photographing processing. In this case, for example, the processor 70 may cause the monitor 90 to display a checking screen for checking with the examiner whether or not to employ a template determined that the distortion is out of the allowable range. In a state where the checking screen is displayed, the image processing device 80 may delete the template by receiving an input operation for refusing to use the template. After the deletion, the template may be re-photographed manually or automatically.

On the checking screen, for example, a composite image of the template and the comparison image may be displayed on the monitor 90. The composite image may be an image in which the comparison image and the template are superimposed. As a specific example, it may be an image in which the comparison image and the template are represented by different color channels with each other. Further, it may be an image in display format of check pattern in which the comparison image and the template are alternately and repeatedly disposed (for example, see "JP-A-2013-15421" by the present applicant).

In the present embodiment, the template distortion correction processing (S15) may be performed based on the comparison image. The distortion correction processing may be, for example, a non-rigid registration or a rigid registration. For the non-rigid registration, for example, a method described below can be adopted. By performing the distortion correction processing, it is possible to obtain an image in which distortion of the comparison image is further reduced as a template for the photographed image.

Further, the template may be an added image by a plurality of fundus images. When the channel is different between the template and the comparison image (or when the wavelength range of the illumination light is different), it is conceivable a case where different features are depicted between the template and the comparison image. In this case, when the distortion correction of a plurality of templates is performed based on the comparison image, a case where distortion is not properly corrected in a part of the plurality of templates is likely to occur. In this case, as a result, the channel difference may cause noise in a composite image using the template after the distortion correction. Therefore, for example, one of the templates for which the distortion correction is completed with respect to the comparison image may be used as a fourth template, and the distortion correction of the remaining photographed images may be performed based on the fourth template. Since the fourth template and another photographed image have the same channel, the noise is easily suppressed.

<Detailed Description of Photographing Processing>

In the example in FIG. 3, after the template is acquired as described above, the photographing processing (S5) is executed.

Figure 6:
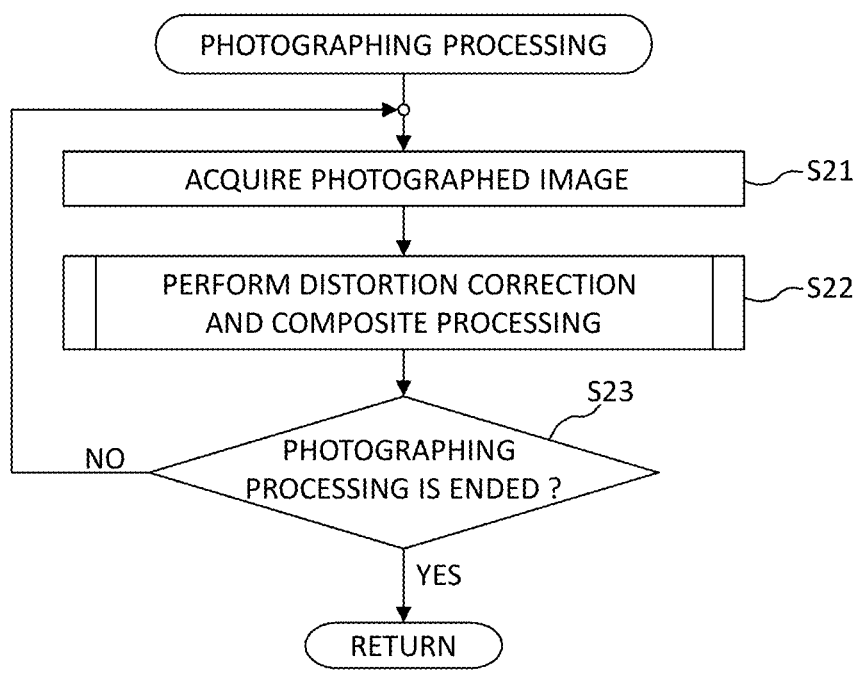
FIG. 6 is a flowchart for explaining the photographing processing.

Here, the photographing processing (S5) according to the embodiment will be described in detail with reference to FIG. 6. In the photographing processing, a photographed image is captured as described above (S21). In the captured photographed image, in a distortion correction and composite processing (S22), at least two-dimensional distortion caused by the movement of the eye during the photographing is corrected based on the template.

At this time, in the present embodiment, by the local matching, the corresponding points or the corresponding regions between the image of the subject eye and the template are set at a plurality of positions of each of the images of the subject eye and the templates, and a movement amount (also referred to as a displacement amount) for each corresponding point or each corresponding region is calculated. Then, the entire photographed image is deformed based on the movement amount for each corresponding point or each corresponding region acquired by the local matching. At this time, the photographed image may be non-rigidly deformed (non-rigid registration). Thereby, the distortion (two-dimensional distortion) in the photographed image is corrected. In the present embodiment, the photographed image in which the distortion is corrected is composited to the template. At this time, for example, the processing of S21 and S22 may be repeated until a predetermined number of photographed images are composited. Alternatively, the image quality of the composite image may be evaluated each time a new photographed image is composited, and the photographing processing (S5) may be ended at the stage an evaluation value of the image quality exceeds a threshold value. By such a photographing processing, a composite image using the plurality of photographed images is obtained as a photographing result. The composite image may be, for example, an added image using the plurality of photographed images. The composite image may be stored in the memory 75 or displayed on the monitor 90 as a photographing result.

<First Distortion Correction and Composite Processing>

First, the flow of the first distortion correction and composite processing applicable in the present embodiment will be described with reference to FIG. 7. In the first distortion correction and composite processing, the template image and the photographed image are divided into a plurality of blocks (also referred to as divided regions), and the movement amount between corresponding blocks between the two images is calculated (local matching). Then, based on the movement amount of each block, the entire photographed image is non-rigidly deformed. The block mentioned here is an example of a corresponding region set at a plurality of positions of each of the template images and the photographed images.

Figure 7:
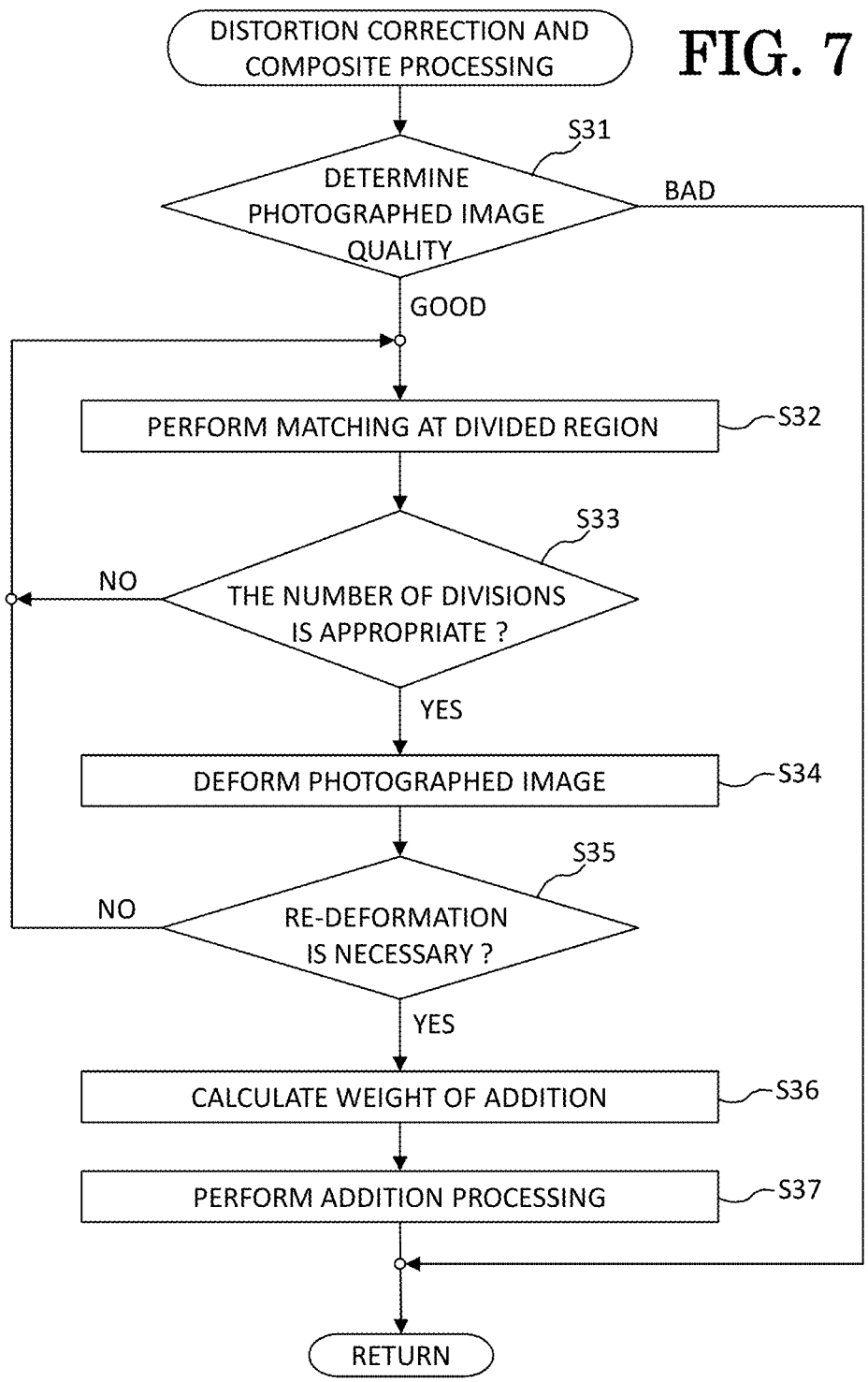
FIG. 7 is a flowchart for explaining a first distortion correction and composite processing.

In FIG. 7, it is determined whether or not the photographed image captured immediately before (by the processing in S21) is an image suitable for a distortion correction (S31) based on the global matching. The global matching in the present embodiment is processing for substantially aligning the template image and the photographed image. For example, the global matching may be a matching between the entire images, or may be a matching using only a part of region (for example, a central region) of the image. When the maximum value of the similarity degree (for example, correlation) in the global matching is equal to or greater than a predetermined threshold value, the photographed image may be determined to be an image suitable for correction (S41: GOOD). When the similarity degree is equal to or less than the threshold value, the photographed image may be determined to be unsuitable for the correction (S41: BAD). In the latter case, the first distortion correction and composite processing may be ended without adding the photographed image that is captured immediately before to the template.

Figure 8A:
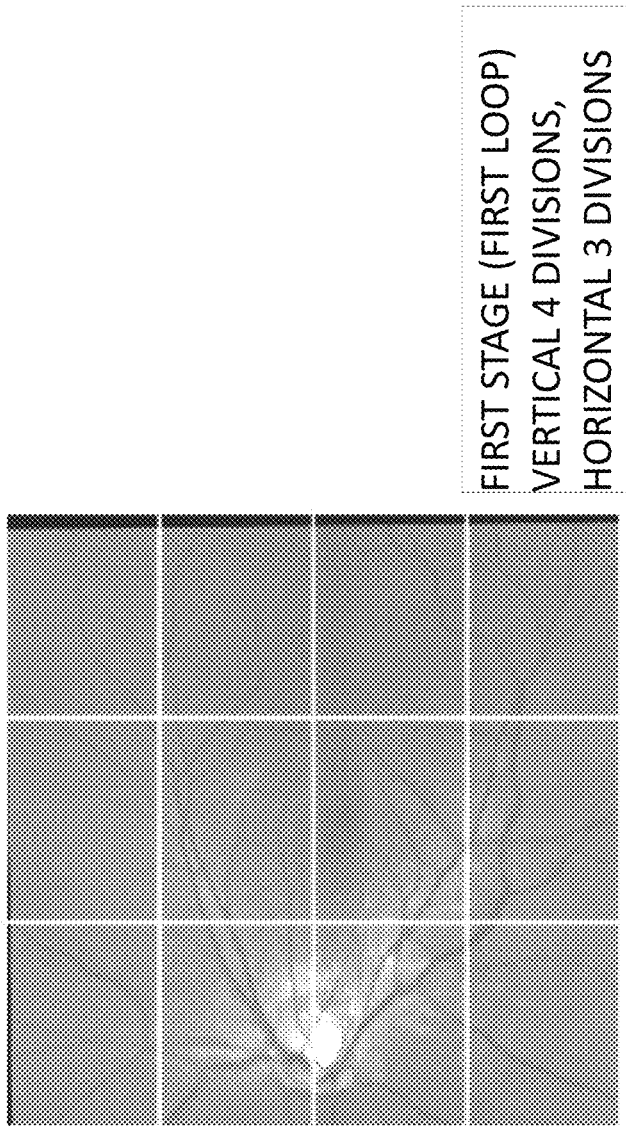
FIG. 8A illustrates an example of a case where the template is divided.

Next, the local matching is performed by the image processing device 80 (S32). The template image and the photographed image are each divided into a plurality of blocks (also referred to as divided regions and corresponding regions), and the matching is performed between the corresponding blocks. As an example, as illustrated in FIG. 8A, it may be divided into twelve blocks, which are horizontally divided into three equal parts and vertically into four equal parts. For example, the matching may be performed for each block, and the maximum value of the similarity degree (for example, correlation by POC) and the movement amount when the similarity degree is maximized may be obtained for each block.

The distortion of the image is reflected on the movement amount of each block. Therefore, the more finely the block is divided, the more accurately the distortion can be detected. On the other hand, the processing load increases as the blocks become finer. Therefore, in the present embodiment, the result of matching is evaluated after division, and the number of divisions is increased stepwise (recursively) according to the result of matching, in this way, it is possible to achieve both accuracy and reduction in processing load. As an example, it is determined whether or not the number of divisions is appropriate based on the similarity degree for each block (S33). For example, when the number of blocks in which the maximum value of the similarity degree exceeds the threshold value is equal to or more than a predetermined number, the number of divisions may be determined to be appropriate (sufficient) (S33: YES). On the other hand, when the maximum value of the similarity degree is less than the threshold value, the number of divisions may be determined to be inappropriate (insufficient) (S33: NO). In this case, in the present embodiment, the image is divided into further smaller blocks (S32), and the matching is performed again (S33). For example, the number of divisions may be increased stepwise in the flow of FIG. 8A (first stage: vertical 4 divisions, horizontal 3 divisions)→FIG. 8B (second stage: vertical 8 divisions, horizontal 3 divisions)→FIG. 8C (third stage: vertical 12 divisions, horizontal 3 divisions)→and so on.

Figure 8B:
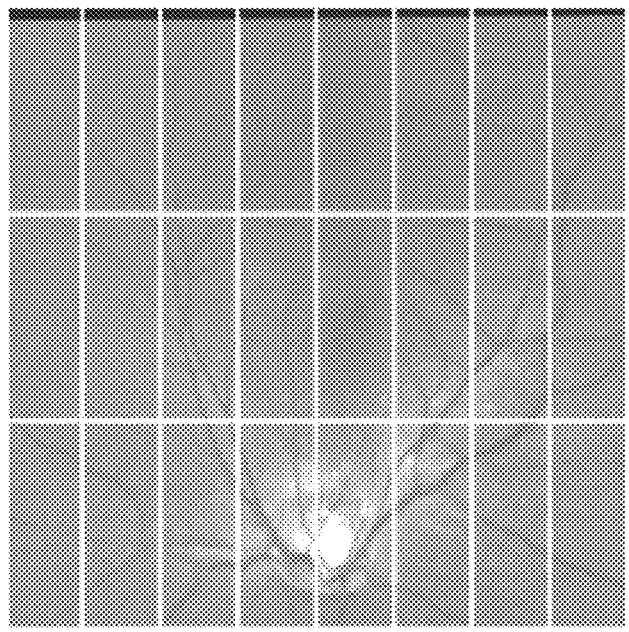
FIG. 8B illustrates an example of a case where the template is divided, and illustrates a case where the template is divided in more detail than FIG. 8A.
Figure 8C:
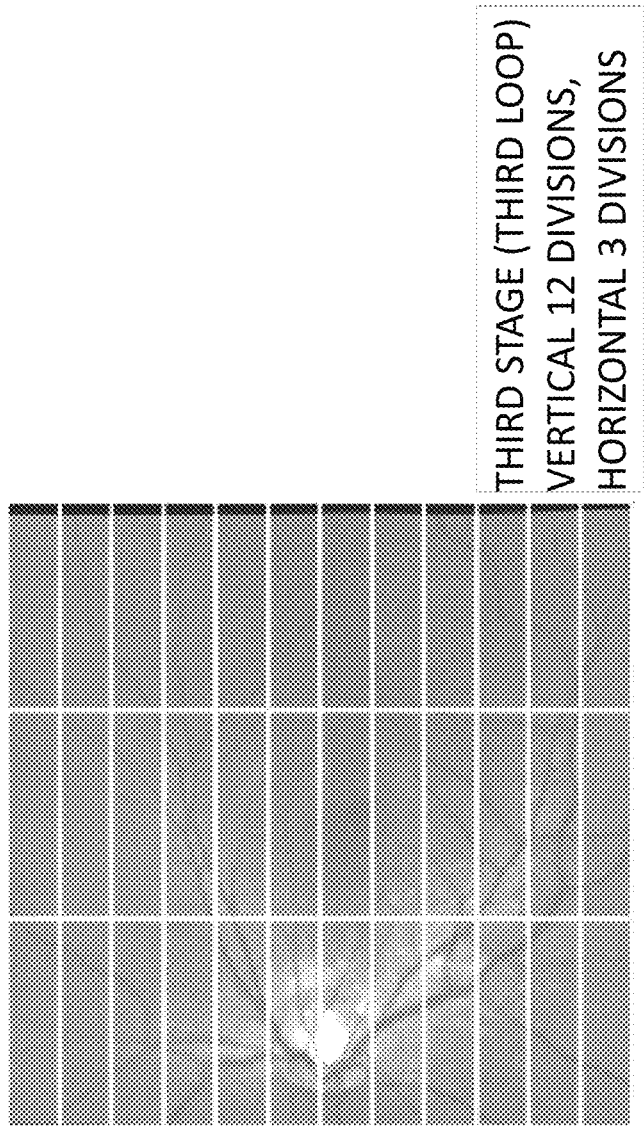
FIG. 8C is an example of a case where the template is divided, and illustrates a case where the template is divided in more detail than FIG. 8B.

In the present apparatus 1, since the scan speed in the horizontal direction (main scanning direction) is much faster as compared with the vertical direction (sub-scanning direction), the distortion hardly occurs in each of the main scanning lines. Therefore, it is preferable that the number of divisions in the sub-scanning direction is larger as compared with the number of divisions in the horizontal direction (main scanning direction). Further, each of the blocks may be formed to be long in the horizontal direction (in other words, the horizontal direction is taken as the longitudinal direction). In FIGS. 8A to 8C, each block is formed as a rectangle where the longitudinal direction is set to the horizontal direction. In order to detect distortion due to the rotation component, it is preferable that the block is divided into two or more blocks in the horizontal direction. In FIGS. 8A to 8C, the number of divisions in the horizontal direction is not increased stepwise as in the case of the number of divisions in the vertical direction. However, it is not necessarily limited to this, and the number of divisions in the horizontal direction may be increased stepwise.

Next, the photographed image is deformed non-rigidly (non-linearly) based on the movement amount of each block in the final divided state (S34). As a non-rigid deformation algorithm, various methods such as a thin plate spline method and a B-spline method are known. In the present embodiment, any one of various methods can be appropriately applied. For example, when the thin plate spline method is applied, the center of each block is moved based on the movement amount, and the movement of other points is moved by thin plate spline interpolation. As a result, the entire photographed image may be deformed.

Next, it is determined whether or not re-deformation is necessary (S35). For example, the image processing device 80 may obtain the similarity degree between the template and the photographed image after the distortion correction and determine whether or not re-deformation is necessary based on the similarity degree. The similarity degree can be evaluated by, for example, a mutual information amount between two images.

Here, when it is determined that re-deformation is necessary (S35: YES), the processing of S32 to S35 are repeated after increasing the number of divisions of the photographed image. For convenience, the number of times in repetitions is counted as a first loop, a second loop, a third loop, and so on. An upper limit may be set for the number of times the processing is repeated. In the example illustrated in FIG. 9, the processing can be repeated up to the third loop at the maximum.

For example, the above determination may be performed based on a comparison between a value indicating the similarity degree and a predetermined threshold value. When the value indicating the similarity degree is equal to or greater than the threshold value, it may be determined that re-deformation is unnecessary.

Figure 9:
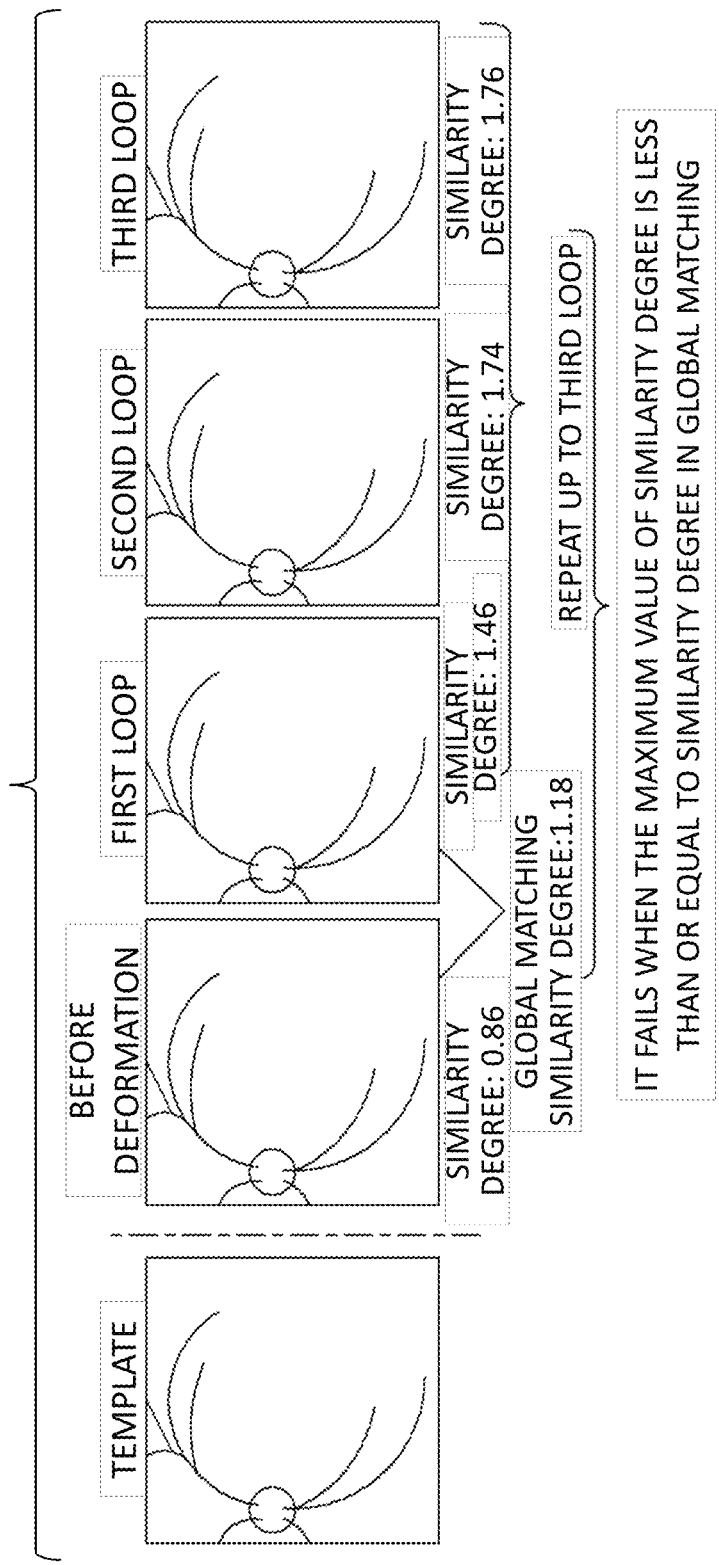
FIG. 9 is a diagram illustrating determination processing whether or not a re-deformation is necessary for an image of a subject eye after a distortion correction.
Figure 10:
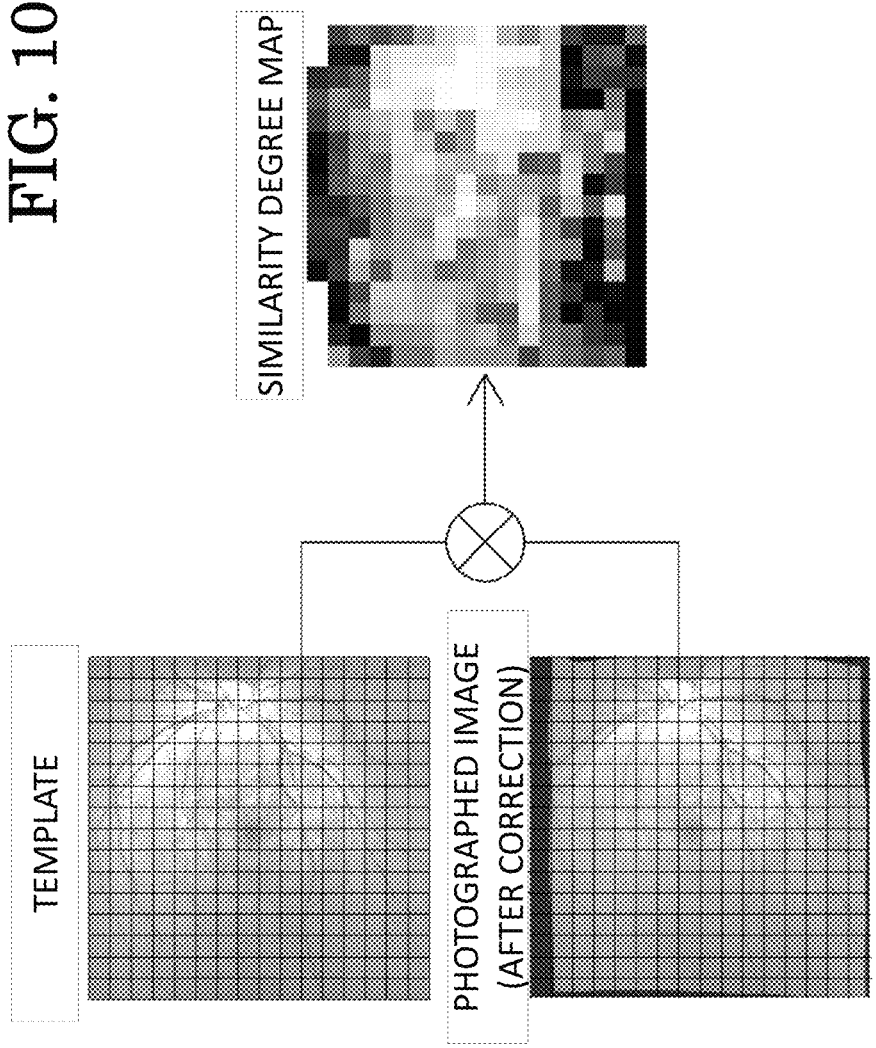
FIG. 10 is a diagram for explaining a calculation method of a weighting coefficient for addition based on a similarity degree.

On the other hand, when the value indicating the similarity degree falls below the threshold value, it may be determined that re-deformation is necessary. In this case, for example, an image in which the value indicating the similarity degree takes the maximum value by repeating the processing up to the third loop at the maximum may be adopted as a target of the composite processing with another photographed image. However, since the distortion correction is not always performed correctly in an image having the similarity degree which takes the maximum value, a second threshold value that defines a lower limit of the similarity degree is compared and when the similarity degree exceeds the second threshold value, the image having the similarity degree which takes the maximum value may be adopted. In the example of FIG. 9, the similarity degree between the photographed image before the deformation and the image after the distortion correction in the first loop is used as the second threshold value. In FIG. 9, the similarity degree 1.18 is used as the second threshold value. When the maximum value of the similarity degree when the processing is repeated up to the third loop at the maximum does not exceed the second threshold value, it is considered that the distortion correction fails. In this case, none of the images is adopted as a target of the composite processing with another photographed image.

Regarding the photographed image after the distortion correction which is adopted as the target of the composite processing, a weighting calculation of addition is performed (S36). The weighting calculation is performed for each region of the image. For example, the template and the photographed image after the distortion correction are divided into a plurality of blocks in each of the vertical and horizontal directions (in FIG. 10, divided into 16 in each of the vertical and horizontal directions), and the similarity degree of the corresponding block between the images may be obtained. At this time, the position of each block is matched in each image. The similarity degree of the corresponding block may be evaluated by, for example, a zero-mean normalized cross-correlation (ZNCC), or may be evaluated by another similarity degree. The weighting coefficient of each block may be calculated according to the similarity degree of each block.

The calculated weighting coefficient is applied to each region of the photographed image after the distortion correction, and the photographed image is added to another image (S37). A region in which a large amount of distortion with respect to the template remains is added with a smaller weighting coefficient. As a result, it is possible to suppress the influence of the region where a large amount of distortion remains in the composite image.

As described above, the first distortion correction and composite processing may be performed.

<Second Distortion Correction and Composite Processing>

Next, a flow of the second distortion correction and composite processing applicable in the present embodiment will be described based on FIG. 11.

In the second distortion correction and composite processing, a plurality of control points (reference points) are set on a plurality of scanning lines in the template. Although the details differ in a part, the movement amount (deviation amount) of the control point (that is, the corresponding point) between the template and the photographed image is obtained by the local matching of the small region including each control point. In the second distortion correction and composite processing, the method of weighting addition is largely different from the second distortion correction and composite processing. In the second distortion correction and composite processing, in each line, the movement amount of the control point is fitted by a predetermined function, and the weighting coefficient is derived in consideration of the fitting error of each control point and the change of the movement amount with respect to the adjacent line. Hereinafter, the details will be described.

Figure 11:
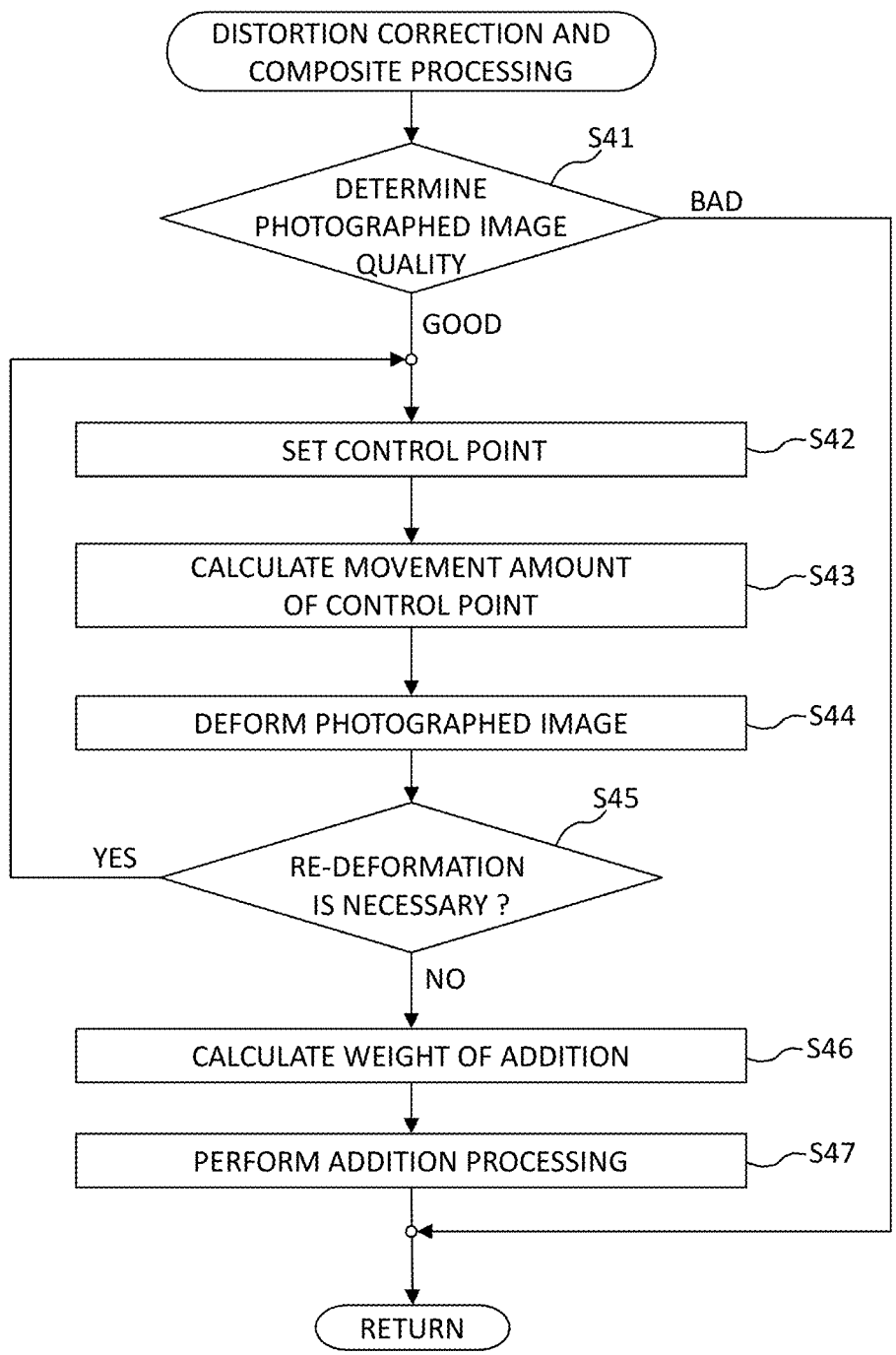
FIG. 11 is a flowchart for explaining a second distortion correction and composite processing.
Figure 12:
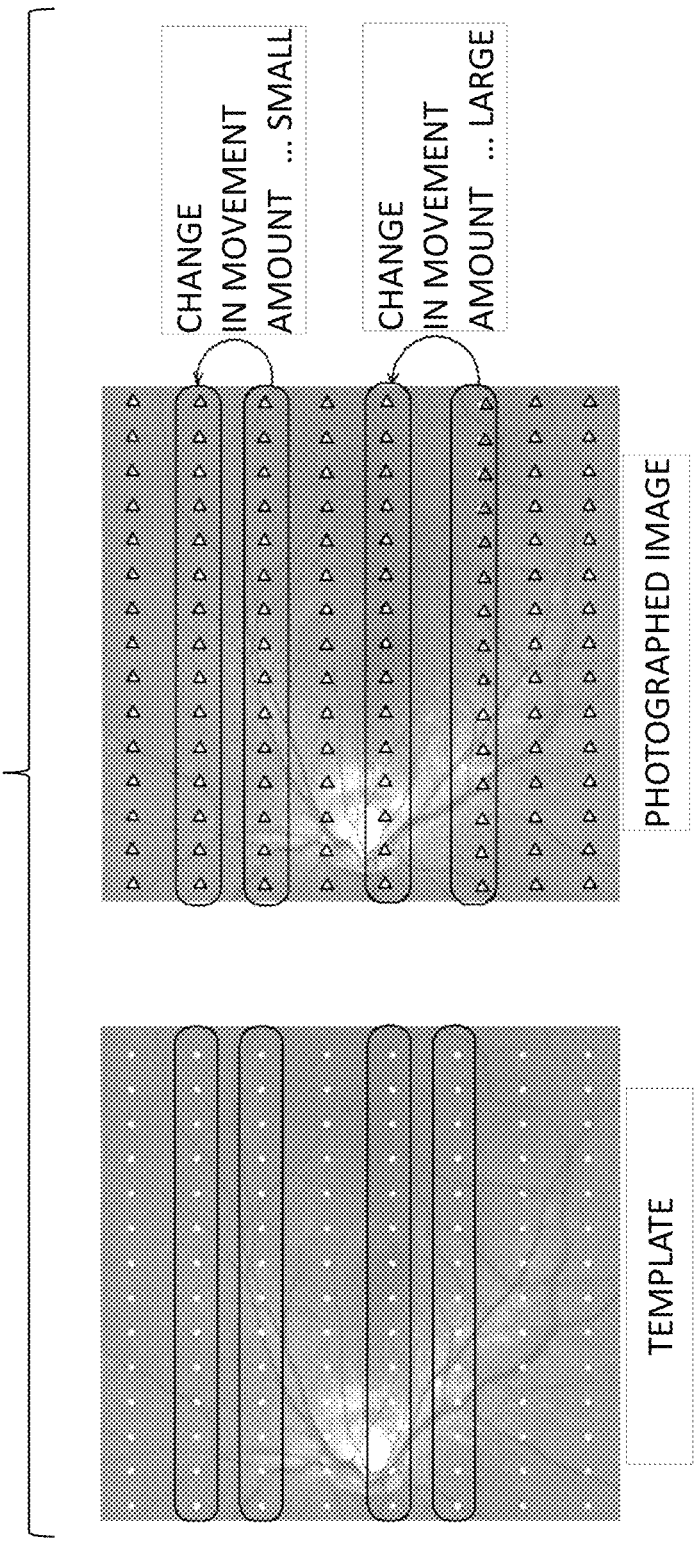
FIG. 12 is a diagram illustrating an example of an arrangement form of control points (corresponding points) in the second distortion correction and composite processing.

In FIG. 11, first, it is determined whether or not the photographed image is an image suitable for the distortion correction (S41). This processing may be the same as the processing in S31 in the first distortion correction and composite processing, and thus detailed description will be omitted.

Next, a plurality of control points are set on the template by the image processing device 80 (S42). The plurality of control points are sot for each of a plurality of lines (main scanning lines).

The line on which the control point is set may be determined in advance. As an example, in FIG. 12, the control points (indicated by a circle mark in FIG. 12) are set on eight scanning lines arranged at equal intervals.

After the control points are set, the local matching is performed. Specifically, the movement amount of each control point between the template and the photographed image is calculated (S43). For example, based on the local matching by a small region including a control point, a position of a point corresponding to the control point in the template (that is, a control point on the photographed image side, indicated by a triangle mark in FIG. 12) is searched, and the movement amount of both may be calculated. The small region may be a region of a predetermined size centered on the control point.

Figure 13:
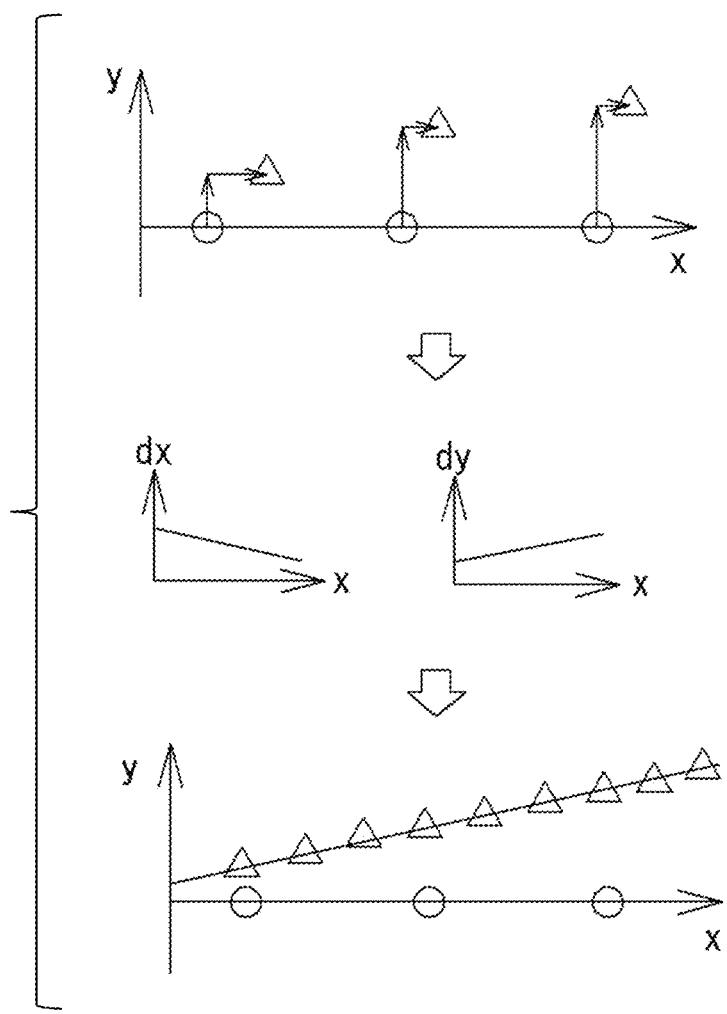
FIG. 13 is a diagram illustrating an overview of a fitting curve of a movement amount.
Figure 14A:
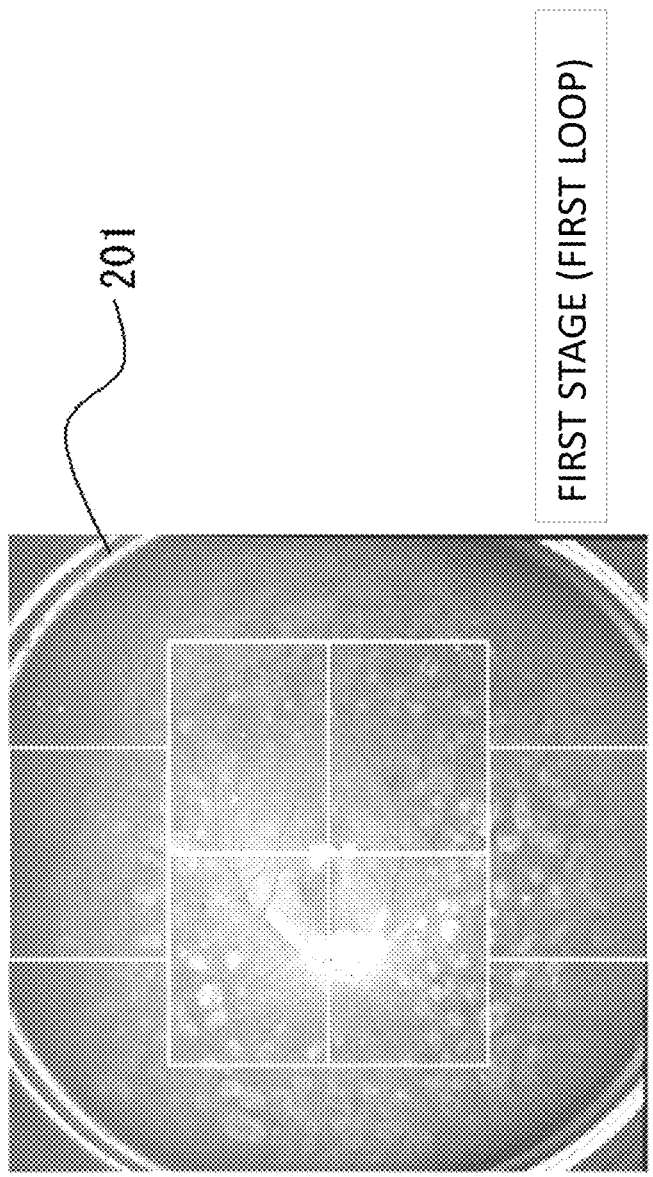
FIG. 14A is a diagram illustrating an example of division form when the distortion correction and composite processing are applied to a photographed image having a wide angle of view.
Figure 14B:
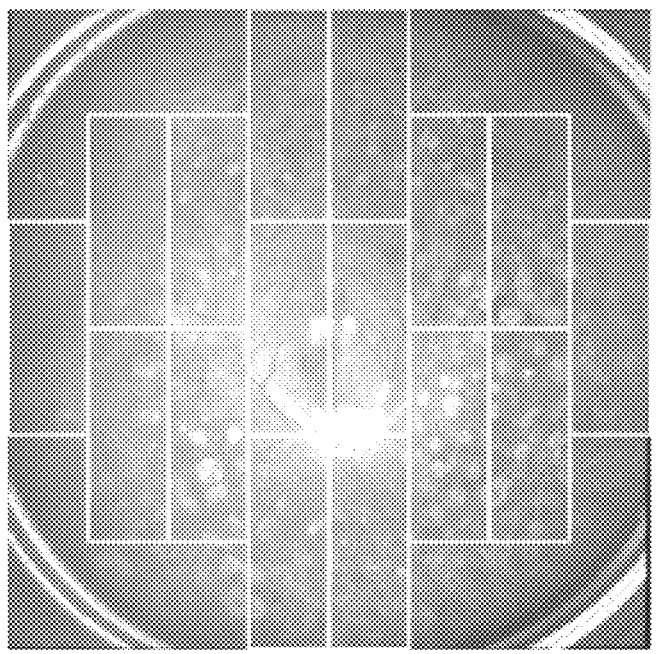
FIG. 14B illustrates when the division is performed in more detail than in FIG. 14A.
Figure 14C:
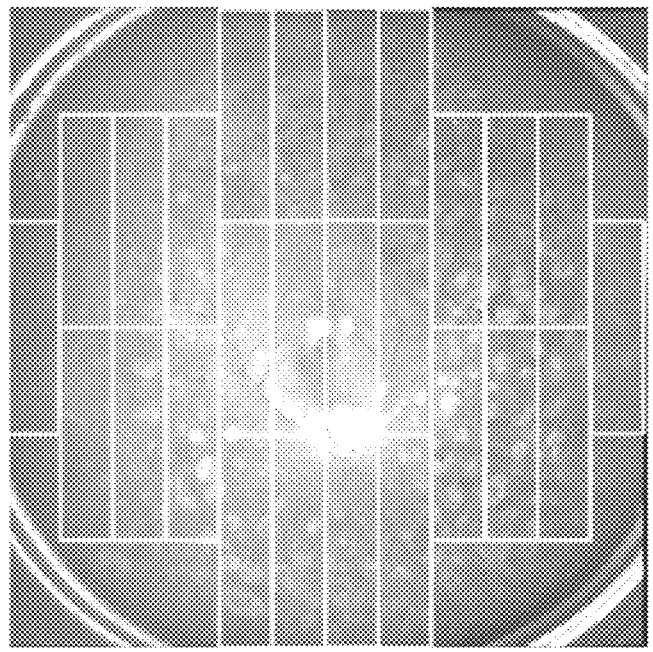
FIG. 14C illustrates when the division is performed in further more detail than FIG. 14B.

In the processing in S43, the movement amount may be calculated for each line. As illustrated in FIG. 13, for example, the movement amounts of the plurality of control points in one line may be fitted by a function. Any fitting methods may be selected from various methods such as least-squares approximation. In this case, as illustrated in FIG. 13, it may be considered that there is a corresponding point on the fitting curve with each point on the line including each control point. The function has, for example, a position x in the main scanning direction and a position y in the sub-scanning direction as variables.

Next, the photographed image is non-linearly (non-rigidly) deformed based on the movement amount calculated for each control point or each line where the control point is set (S44). For example, the photographed image may be deformed by the thin plate spline method, or the photographed image may be deformed by another method.

Next, it is determined whether or not re-deformation is necessary (S45). This processing may be the same as the processing in S35 in the first distortion correction and composite processing, and thus detailed description will be omitted. When it is determined that the re-deformation is necessary, the control points are increased, and the processing of S42 to S45 is repeated (looped). In this case, it is preferable to set more control points by increasing the lines on which the control points are set. The larger the distortion, the more easily the photographed image is deformed based on a large amount of control points, and thus distortion is easily corrected well.

Next, the weighting calculation of addition is performed (S46), and addition processing is performed using the calculated coefficients (S47). As with the First distortion correction and composite processing, the weighting coefficient may be calculated based on the similarity degree of each region between the template and the photographed image after the distortion correction.

Further, in the second distortion correction and composite processing, the weighting coefficient may be calculated based on the magnitude of the error between the above-described fitting curve with respect to the control point of each line on the photographed image and the control point (hereinafter, referred to as "fitting error"). Regarding the lines with large errors, it is considered that a large distortion is included in the template or an artifact due to vignetting or the like exists. Therefore, for example, when the sum of the errors of the control points in a certain line is equal to or greater than a threshold value, a weighting coefficient that is not used for addition to another photographed image may be given to the line and its periphery. The weighting coefficient based on the error between the fitting curve and each control point is referred to as a degree of abnormality for convenience.

Further, the weighting coefficient may be calculated based on the magnitude of a change (difference) in the movement amount between lines adjacent to each other where the control point is set for each of the plurality of lines. When the change in the movement amount is large, it is considered that there is a change in eye movement during the scanning of the adjacent line, and distortion occurs. Accordingly, for example, a smaller coefficient may be given as the change (difference) of the movement amount is larger. The weighting coefficient based on the magnitude of the change (difference) in the movement amount between adjacent lines is referred to as reliability for convenience.

The coefficient based on the similarity degree, the degree of abnormality, and the reliability can be multiplied. That is, two or more of these coefficients can be simultaneously applied to each region of the photographed image after the distortion correction. By performing the addition processing using two or more coefficients, a favorable added image in which the influence of distortion is further suppressed is easily obtained.

<Distortion Correction of a Plurality of Channels Photographed Simultaneously in Subject Eye>

In the case of performing the distortion correction with respect to the image of each channel in the images of the subject eye of a plurality of channels photographed at the same time, it is not always necessary to perform the above processing for each channel. For example, the above processing is performed on any one channel, and the correction amount and the weighting coefficient of the distortion correction calculated on one channel are applied to the images of another channel photographed at the same time.

<Setting of Corresponding Region or Corresponding Point to Avoid Internal Reflection Image>

For example, it is conceivable that the internal reflection images of the imaging optical systems 10 and 20 are reflected in the photographing range. The internal reflection image is generated when the illumination light is reflected by the optical members included in the imaging optical systems 10 and 20. The internal reflection image is, for example, an artifact due to reflection on the optical member included in the imaging optical system. The internal reflection image appears at a fixed position on the image regardless of the movement of the eye. Therefore, the image processing device 80 may arrange a plurality of blocks (corresponding regions) or control points (corresponding points) in the first or second distortion correction and composite processing, avoiding the internal reflection image. As a result, the corresponding region or corresponding point between the template and the photographed image is set by excluding the element that is stationary regardless of the movement of the eye, so that the accuracy of the distortion correction based on the movement amount of the corresponding region or the corresponding point is improved.

<Adjustment of Corresponding Point and Corresponding Point According to Angle of View and Resolution>

Further, for example, parameters relating to blocks (corresponding regions) in the first distortion correction and composite processing, and parameters relating to control points (corresponding points) in the second distortion correction and composite processing may be adjusted by the image processing device 80 depending on the angle of view, the number of pixels, or both, of the photographed image. A parameter that can be adjusted relating to the block (divided region) may be, for example, at least one of the number, size, arrangement, and shape of the block. Further, a parameter that can be adjusted relating to the control point may be at least one of the number (density) and an arrangement.

For example, it is considered that as the number of pixels increases, the photographing time is longer, and the photographed image is more likely to be affected by distortion. On the other hand, as the number of pixels increases, the number of blocks or control points may be increased. That is, the corresponding points between the template and the photographed image in the local matching may be increased as the number of pixels of the photographed image increases. Thereby, it becomes easy to perform the correction processing with respect to the distortion of the photographed image with an appropriate processing load.

Further, for example, in FIGS. 13A to 13C, as a result of the angle of view of the photographed image being increased by the angle of view switching portion, it is conceivable that the edge of the objective optical system (the edge of the lens 201 in FIGS. 13A to 13C) is reflected on the image as an internal reflection image. In this case, the tissue of the subject eye is depicted in a region inside the edge, and distortion due to the eye movement may occur in the region. On the other hand, no distortion can occur in the edge and the region outside the edge. Therefore, when the edge of the optical system is included in the photographing range, the image processing device 80 may arrange a plurality of blocks or control points only in the region inside the edge. That is, the image processing device 80 may change the plurality of blocks or control points according to the angle of view to avoid internal reflection image that is generated at a specific angle of view and arrange the plurality of blocks or control points.

<Modification Examples>

As described above, the description has been given based on the embodiment. However, in implementing the present disclosure, the content of the embodiment can be appropriately changed.

<Matching by Using Reduced Image>

For example, a reduced image having a reduced image size may be used for at least one of the various types of matching, and the distortion correction and composite processing in the above embodiment. In this case, a reduced image is generated by reducing the fundus image that is a target of the image processing based on the template. Additionally, a reduced image of the template may be generated. By performing the image processing with the reduced size, the processing load on the image processing device 80 is reduced. The correspondence between each pixel in the reduced image and each pixel in the original image is uniquely determined by the magnification at the time of reduction. The image processing device 80 applies the parameters or the deformation matrix obtained by the matching with the reduced size to the fundus image of the original size at the above magnification. As a result, various types of matching, and the distortion correction and composite processing can be executed with a lower processing load (in other words, faster).

<Application of Various Types of Image Processing in Scenes Other than Capturing>

In the above embodiment, various types of processing by the image processing device 80 are executed when capturing a photographed image. However, it is not limited to this, and various types of image processing may be executed on the fundus image captured in advance by the image processing device 80. For example, the execution timing of all or a part of <template acquisition processings>, <distortion detection processing and determination processings>, <first and second distortion correction and composite processing>, or the like may be at the time of brow sing, not at the time of photographing.

When various types of image processing is performed on a fundus image captured in advance, at least one of various types of templates and a fundus image to be composited to the template may be selectable from a plurality of fundus images that are photographed in advance based on an operation input from the examiner.

In this case, a selection screen may be displayed on the monitor 90. It is preferable that at least two fundus images among the plurality of fundus images are displayed side by side on the selection screen. Further, the displayed image may be arbitrarily replaceable with another image. Thereby, the examiner can compare the plurality of fundus images well. Then, an image photographed well can be easily selected as a target of image processing.

<Manual Setting of Corresponding Point or Corresponding Region>

In the above-described embodiment, a case has been described in which the corresponding point or the corresponding region (the parameter relating to the corresponding point or the corresponding region) is automatically and appropriately set with respect to the template and the photographed image. However, it is not necessarily limited to this, and it may be set manually based on the operation input by the examiner. The setting here includes not only the case of setting based on zero, but also a modification of the automatically set corresponding point and corresponding region (parameter related to the corresponding point or corresponding region) based on the operation input.

In this case, regarding the corresponding point, at least one parameter of the number (density) and the arrangement may be settable based on the operation input. Further, regarding the corresponding region, at least one parameter among the number, the size, the arrangement, and the shape may be settable based on the operation input. When the corresponding point or the corresponding region is manually set, various types of processing such as local matching are executed by the image processing device 80, similarly to the case where the corresponding point or the corresponding region is automatically set. The parameter may be arbitrarily settable by the examiner and selectable any one of a plurality of predetermined patterns in accordance with the operation input, and both may be used together.

When the corresponding point or the corresponding region is manually set, the setting state of the corresponding point or the corresponding region may be checkable by a graphical display. For example, a fundus image (for example, a template) on which an index indicating a corresponding point or a corresponding region is superimposed may be displayed on the monitor 90 for checking.

<Application to OCT>

In the above-described embodiment, the ophthalmologic imaging apparatus is an apparatus that photographs a front image (two-dimensional image) of the fundus by a scanning-type imaging optical system, but is not necessarily limited to this. For example, the technology of the present disclosure is also applicable to an optical coherence tomography (hereinafter, referred to as OCT) that photographs a tomographic image of a subject eye. In the case of OCT, the imaging optical system may include an OCT optical system (not shown) that acquires OCT data of the fundus based on a spectral interference signal between the return light and the reference light. Alternatively, the imaging optical system in the ophthalmologic imaging apparatus may include both the front imaging optical system (for example, the imaging optical systems 10 and 20 in the above embodiment) and the OCT optical system.

<Partial Implementation of Above-Described Embodiment>

"Template acquisition processing" and "photographing processing" in the above-described embodiment can be independent, and it is not always necessary that both are implemented integrally. For example, for the template utilized in the "photographing processing", it is not always necessary to perform distortion detection or distortion correction using the comparison image. Further, only "template acquisition processing" may be performed.

What is claimed is:

1. An ophthalmological image processing apparatus, comprising:
   a processor,
   wherein when an ophthalmological image processing program is executed by the processor, the processor executes:
      acquisition processing of acquiring a plurality of images of a subject eye photographed by a scanning-type imaging optical system;
      local matching of, by utilizing any one of the plurality of images of the subject eye as a template, setting corresponding points or corresponding regions between an image of the subject eye and the template at a plurality of positions of each of the image of the subject eye and the template, and calculating a movement amount of each of the corresponding points or each of the corresponding regions; and
      distortion correction processing of correcting a distortion of the image of the subject eye with respect to the template based on the movement amount of each of the corresponding points or each of the corresponding regions; and
   wherein in the distortion correction processing, the processor deforms the image of the subject eye non-rigidly.

2. The ophthalmological image processing apparatus according to claim 1,
   wherein in the local matching, the processor sets a plurality of the corresponding points or the corresponding regions respectively in a vertical direction and a horizontal direction of the image of the subject eye.

3. The ophthalmological image processing apparatus according to claim 2,
   wherein in the local matching, the processor sets a plurality of the corresponding points for each of a plurality of lines along a main scanning line in the template.

4. The ophthalmological image processing apparatus according to claim 1,
   wherein in the local matching, the processor obtains a similarity degree between the image of the subject eye and the template for each of the corresponding points or each of the corresponding regions, and sets the corresponding points or the corresponding regions to be more dense according to the similarity degree to execute the local matching again.

5. The ophthalmological image processing apparatus according to claim 1,
   wherein the processor compares an image of the subject eye after a distortion correction with the template, and sets the corresponding points or the corresponding regions to be more dense according to a comparison result to execute the local matching and the distortion correction processing again.

6. The ophthalmological image processing apparatus according to claim 1,
   wherein in the local matching, the processor changes a parameter related to the corresponding point or the corresponding region according to an angle of view in the image of the subject eye.

7. The ophthalmological image processing apparatus according to claim 1,
   wherein in the local matching, the processor arranges the corresponding point or the corresponding region while avoiding an internal reflection image of the imaging optical system in the image of the subject eye.

8. The ophthalmological image processing apparatus according to claim 1,
   wherein the processor further executes number-of-pixels setting processing of changing the number of pixels in the image of the subject eye, and
   in the local matching, the processor changes a parameter related to the corresponding point or the corresponding region according to the number of pixels.

9. The ophthalmological image processing apparatus according to claim 1,
   wherein the processor further executes composite processing of obtaining a composite image by compositing a plurality of images of the subject eye after a distortion correction.

10. The ophthalmological image processing apparatus according to claim 9,
    wherein the processor calculates a similarity degree for each region between the image of the subject eye after the distortion correction and the template, and calculates a composite weighting coefficient in the composite processing for each region according to the similarity degree.

11. The ophthalmological image processing apparatus according to claim 9, wherein the processor,
    in the local matching, sets a plurality of the corresponding points for each of a plurality of lines along a main scanning line in the template, and
    obtains a fitting curve of a movement amount for each of the lines based on the movement amounts of the plurality of the corresponding points in the image of the subject eye, and calculates a composite weighting coefficient in the composite processing for each line according to the movement amounts of the plurality of the corresponding points included in the line and an error between the fitting curve and the plurality of the corresponding points included in the line.

12. The ophthalmological image processing apparatus according to claim 9, wherein the processor, in the local matching, sets a plurality of the corresponding points for each of a plurality of lines along a main scanning line in the template, and calculates a composite weighting coefficient in the composite processing for each line based on a change in the movement amounts of the corresponding points between the plurality of the lines.

13. The ophthalmological image processing apparatus according to claim 1, wherein the plurality of the images of the subject eye acquired in the acquisition processing are continuously photographed based on one release signal.

14. The ophthalmological image processing apparatus according to claim 1, wherein the plurality of the images of the subject eye acquired in the acquisition processing includes a first image being an image of the subject eye photographed under a first condition and a second image being an image of the subject eye photographed under a second condition, which is set to be less distorted than the first condition, at a timing different from a timing of photographing the first image, and the processor utilizes the second image as the template in the local matching.

15. The ophthalmological image processing apparatus according to claim 14, wherein when the second image is utilized as the template, the processor further executes at least one of distortion detection processing of the first image with respect to the second image and the distortion correction processing in advance.

16. The ophthalmological image processing apparatus according to claim 14, wherein the first condition is a condition for acquiring a photographed image with visible light as the first image, and the second condition is a condition for acquiring an observation image with infrared light as the second image.

17. The ophthalmological image processing apparatus according to claim 14, wherein the second condition has a period of time for scanning a photographing range of the subject eye with light shorter than that of the first condition.

18. The ophthalmological image processing apparatus according to claim 1, wherein the image of the subject eye is a fundus front image of the subject eye.

19. The ophthalmological image processing apparatus according to claim 18, wherein the image of the subject eye is photographed at an angle of view of 80° or more.

20. An ophthalmological image processing apparatus, comprising:

a processor, wherein when an ophthalmological image processing program is executed by the processor, the processor executes:

acquisition processing of acquiring a plurality of images of a subject eye photographed by a scanning-type imaging optical system;

local matching of, by utilizing any one of the plurality of images of the subject eye as a template, setting corresponding points or corresponding regions between an image of the subject eye and the template at a plurality of positions of each of the image of the subject eye and the template, and calculating a movement amount of each of the corresponding points or each of the corresponding regions; and distortion correction processing of correcting a distortion of the image of the subject eye with respect to the template based on the movement amount of each of the corresponding points or each of the corresponding regions; and wherein the plurality of the images of the subject eye acquired in the acquisition processing includes a first image being an image of the subject eye photographed under a first condition and a second image being an image of the subject eye photographed under a second condition, which is set to be less distorted than the first condition, at a timing different from a timing of photographing the first image, and the processor utilizes the second image as the template in the local matching.

* * * * *